US008927691B2

United States Patent
Khan

(10) Patent No.: US 8,927,691 B2
(45) Date of Patent: *Jan. 6, 2015

(54) TRANSDUCIBLE POLYPEPTIDES FOR MODIFYING METABOLISM

(75) Inventor: Shaharyar Khan, Charlottesville, VA (US)

(73) Assignee: Gencia Corporation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/419,189

(22) Filed: Mar. 13, 2012

(65) Prior Publication Data

US 2012/0231521 A1 Sep. 13, 2012
US 2013/0302876 A9 Nov. 14, 2013

Related U.S. Application Data

(63) Continuation of application No. 12/253,138, filed on Oct. 16, 2008, and a continuation-in-part of application No. 13/399,434, filed on Feb. 17, 2012, which is a continuation of application No. 11/932,674, filed on Oct. 31, 2007, now Pat. No. 8,133,733, and a continuation-in-part of application No. 13/171,751, filed on Jun. 29, 2011, now Pat. No. 8,470,972, which is a continuation of application No. 11/930,892, filed on Oct. 31, 2007, now Pat. No. 8,062,891, and a continuation-in-part of application No. 11/389,432, filed on Mar. 24, 2006, now Pat. No. 8,507,277, which is a continuation-in-part of application No. 10/972,963, filed on Oct. 25, 2004, now Pat. No. 8,039,587.

(60) Provisional application No. 60/568,436, filed on May 5, 2004, provisional application No. 60/513,983, filed on Oct. 24, 2003.

(51) Int. Cl.
  *C07K 14/00* (2006.01)
  *C07K 14/435* (2006.01)
  *C12Q 1/68* (2006.01)

(52) U.S. Cl.
  USPC .......... 530/350; 530/388.21; 530/300; 514/1

(58) Field of Classification Search
  None
  See application file for complete search history.

(56) References Cited

U.S. PATENT DOCUMENTS

| | | |
|---|---|---|
| 4,622,302 A | 11/1986 | Sowers |
| 4,752,473 A | 6/1988 | Nayak |
| 4,803,072 A | 2/1989 | Dalton |
| 4,873,089 A | 10/1989 | Scotto |
| 4,901,269 A | 2/1990 | Stoelzle |
| 4,952,496 A | 8/1990 | Studier |
| 5,149,782 A | 9/1992 | Chang |
| 5,166,898 A | 11/1992 | Ishihara |
| 5,422,277 A | 6/1995 | Connelly |
| 5,464,758 A | 11/1995 | Gossen |
| 5,547,932 A | 8/1996 | Curiel |
| 5,552,155 A | 9/1996 | Bailey |
| 5,589,362 A | 12/1996 | Bujard |
| 5,650,298 A | 7/1997 | Bujard |
| 5,654,168 A | 8/1997 | Bujard |
| 5,693,489 A | 12/1997 | Studier |
| 5,709,879 A | 1/1998 | Barchfeld |
| 5,723,319 A | 3/1998 | King |
| 5,728,399 A | 3/1998 | Wu |
| 5,733,540 A | 3/1998 | Lee |
| 5,756,041 A | 5/1998 | Arruda |
| 5,766,626 A | 6/1998 | Gross |
| 5,766,902 A | 6/1998 | Craig |
| 5,770,414 A | 6/1998 | Gage |
| 5,780,444 A | 7/1998 | Kahne |
| 5,789,156 A | 8/1998 | Bujard |
| 5,789,230 A | 8/1998 | Cotten |
| 5,792,645 A | 8/1998 | Beug |
| 5,799,515 A | 9/1998 | Floyd |
| 5,804,445 A | 9/1998 | Brasier |
| 5,814,618 A | 9/1998 | Bujard |
| 5,831,020 A | 11/1998 | Citovsky |
| 5,837,533 A | 11/1998 | Boutin |
| 5,851,796 A | 12/1998 | Schatz |
| 5,859,310 A | 1/1999 | Bujard |
| 5,866,755 A | 2/1999 | Bujard |
| 5,869,320 A | 2/1999 | Studier |
| 5,885,613 A | 3/1999 | Holland |
| 5,888,981 A | 3/1999 | Bujard |
| 5,908,777 A | 6/1999 | Lee |
| 5,912,411 A | 6/1999 | Bujard |
| 5,914,231 A | 6/1999 | Hennink |
| 5,916,803 A | 6/1999 | Sedlacek |

(Continued)

FOREIGN PATENT DOCUMENTS

| | | |
|---|---|---|
| CA | 2272788 | 12/2000 |
| DE | 19856052 | 6/2000 |

(Continued)

OTHER PUBLICATIONS

Alam, at al., 'Human milochondrial DNA is packaged with TFAM', Nucleic Acids Res., 31(6):1640-5 (2003).

(Continued)

*Primary Examiner* — Maria Marvich
(74) *Attorney, Agent, or Firm* — Pabst Patent Group LLP

(57) ABSTRACT

Methods and compositions for modifying the metabolism of a subject are provided. One embodiment provides a recombinant polypeptide having a polynucleotide-binding domain, a protein transduction domain, and a targeting domain. In a preferred embodiment, the polynucleotide-binding domain includes one or more HMG box domains.

5 Claims, 4 Drawing Sheets

(56) References Cited

U.S. PATENT DOCUMENTS

| | | |
|---|---|---|
| 5,922,927 A | 7/1999 | Bujard |
| 5,945,400 A | 8/1999 | Scherman |
| 5,948,681 A | 9/1999 | Scanlin |
| 5,968,773 A | 10/1999 | Heddle |
| 5,981,273 A | 11/1999 | Curiel |
| 5,985,318 A | 11/1999 | Ford |
| 5,985,573 A | 11/1999 | Hennink |
| 6,004,808 A | 12/1999 | Negulescu |
| 6,004,941 A | 12/1999 | Bujard |
| 6,017,734 A | 1/2000 | Summers |
| 6,022,735 A | 2/2000 | Curiel |
| 6,025,192 A | 2/2000 | Beach |
| 6,037,348 A | 3/2000 | Colacino |
| 6,054,312 A | 4/2000 | Larocca |
| 6,063,565 A | 5/2000 | Goodman |
| 6,077,663 A | 6/2000 | Curiel |
| 6,080,791 A | 6/2000 | Bodian |
| 6,087,166 A | 7/2000 | Baron |
| 6,093,537 A | 7/2000 | Goodman |
| 6,099,847 A | 8/2000 | Tobin |
| 6,113,946 A | 9/2000 | Szoka, Jr. |
| 6,120,797 A | 9/2000 | Meers |
| 6,127,159 A | 10/2000 | Fuller |
| 6,127,170 A | 10/2000 | Boutin |
| 6,136,536 A | 10/2000 | Tomkinson |
| 6,136,954 A | 10/2000 | Bujard |
| 6,143,564 A | 11/2000 | Wakayama |
| 6,200,956 B1 | 3/2001 | Scherman |
| 6,207,648 B1 | 3/2001 | Waxman |
| 6,210,708 B1 | 4/2001 | Walti |
| 6,210,717 B1 | 4/2001 | Choi |
| 6,221,665 B1 | 4/2001 | Jaroszeski |
| 6,242,667 B1 | 6/2001 | Bujard |
| 6,246,427 B1 | 6/2001 | Sogabe |
| 6,248,532 B1 | 6/2001 | Keegan |
| 6,251,365 B1 | 6/2001 | Bauerlein |
| 6,251,640 B1 | 6/2001 | Yao |
| 6,252,136 B1 | 6/2001 | Bujard |
| 6,255,071 B1 | 7/2001 | Beach |
| 6,267,987 B1 | 7/2001 | Park |
| 6,270,761 B1 | 8/2001 | Russell |
| 6,271,341 B1 | 8/2001 | Baron |
| 6,271,348 B1 | 8/2001 | Bujard |
| 6,274,322 B1 | 8/2001 | Curiel |
| 6,294,191 B1 | 9/2001 | Meers |
| 6,294,363 B1 | 9/2001 | Madura |
| 6,297,004 B1 | 10/2001 | Russell |
| 6,306,625 B1 | 10/2001 | Jacobs |
| 6,312,727 B1 | 11/2001 | Schacht |
| 6,323,391 B1 | 11/2001 | Schlaepfer |
| 6,337,070 B1 | 1/2002 | Okuno |
| 6,358,524 B1 | 3/2002 | Sedlacek |
| 6,372,720 B1 | 4/2002 | Longmuir |
| 6,379,965 B1 | 4/2002 | Boutin |
| 6,407,178 B1 | 6/2002 | Kolbe |
| 6,410,057 B1 | 6/2002 | Kweon-Choi |
| 6,416,997 B1 | 7/2002 | Mir-Shekari |
| 6,444,871 B1 | 9/2002 | Yao |
| 6,458,026 B1 | 10/2002 | Hart |
| 6,495,346 B1 | 12/2002 | Jerome |
| 6,500,800 B1 | 12/2002 | Sobolev |
| 6,506,559 B1 | 1/2003 | Driver |
| 6,511,676 B1 | 1/2003 | Boulikas |
| 6,531,647 B1 | 3/2003 | Baulcombe |
| 6,544,780 B1 | 4/2003 | Wang |
| 6,586,411 B1 | 7/2003 | Russell |
| 6,632,800 B1 | 10/2003 | Russell |
| 6,633,933 B1 | 10/2003 | Smith |
| 6,652,886 B2 | 11/2003 | Ahn |
| 6,692,911 B2 | 2/2004 | Pack |
| 6,696,038 B1 | 2/2004 | Mahato |
| 6,731,187 B2 | 5/2004 | Kurihara |
| 6,734,171 B1 | 5/2004 | Saravolac |
| 6,737,506 B1 | 5/2004 | Anziano |
| 6,743,781 B2 | 6/2004 | Bischoff |
| 6,759,236 B1 | 7/2004 | Fung |
| 6,759,518 B1 | 7/2004 | Kontermann |
| 6,759,574 B1 | 7/2004 | Ream |
| 6,770,632 B1 | 8/2004 | Aghi |
| 6,771,623 B2 | 8/2004 | Ton |
| 6,780,639 B1 | 8/2004 | Chtarto |
| 6,783,756 B2 | 8/2004 | Bujard |
| 6,835,810 B2 | 12/2004 | Hwu |
| 6,849,272 B1 | 2/2005 | Langer |
| 6,867,036 B1 | 3/2005 | Vile |
| 6,872,406 B2 | 3/2005 | Qi |
| 6,875,448 B1 | 4/2005 | Mayumi |
| 6,878,374 B2 | 4/2005 | Yu |
| 6,897,196 B1 | 5/2005 | Szoka, Jr. |
| 6,903,077 B1 | 6/2005 | Heintz |
| 6,914,124 B2 | 7/2005 | Bujard |
| 6,951,756 B2 | 10/2005 | Lubitz |
| 6,967,197 B2 | 11/2005 | Neya |
| 6,972,650 B2 | 12/2005 | Ma |
| 6,986,902 B1 | 1/2006 | Chen |
| 7,001,768 B2 | 2/2006 | Wolffe |
| 7,018,819 B2 | 3/2006 | Orwar |
| 7,041,312 B2 | 5/2006 | Ehringer |
| 7,042,608 B2 | 5/2006 | Takeuchi |
| 7,048,925 B2 | 5/2006 | Van |
| 7,056,529 B2 | 6/2006 | Ehringer |
| 7,060,291 B1 | 6/2006 | Meers |
| 7,060,461 B2 | 6/2006 | Butt |
| 7,090,837 B2 | 8/2006 | Spencer |
| 7,144,994 B2 | 12/2006 | Anziano |
| 7,202,227 B2 | 4/2007 | Boutin |
| 7,220,576 B2 | 5/2007 | Butt |
| 7,244,435 B2 | 7/2007 | Lai |
| 7,250,299 B1 | 7/2007 | Naldini |
| 7,256,043 B2 | 8/2007 | Hart |
| 7,273,620 B1 | 9/2007 | Zhigaltsev |
| 7,273,722 B2 | 9/2007 | Lin |
| 7,306,944 B2 | 12/2007 | Choi |
| 7,319,086 B1 | 1/2008 | Collyer |
| 7,329,807 B2 | 2/2008 | Vadrucci |
| 7,371,922 B2 | 5/2008 | Wheeler |
| 7,376,128 B2 | 5/2008 | Chen |
| 7,393,478 B2 | 7/2008 | Boulikas |
| 7,393,541 B2 | 7/2008 | Wright |
| 7,402,409 B2 | 7/2008 | Yu |
| 7,410,729 B2 | 8/2008 | Takahashi |
| 7,455,988 B2 | 11/2008 | Fandl |
| 7,456,272 B2 | 11/2008 | Lin |
| 7,459,145 B2 | 12/2008 | Bao |
| 7,498,165 B2 | 3/2009 | Lima |
| 7,521,415 B2 | 4/2009 | Minomi |
| 7,524,648 B2 | 4/2009 | Chen |
| 7,541,446 B2 | 6/2009 | Hillen |
| 7,553,667 B2 | 6/2009 | Hannoufa |
| 7,566,454 B2 | 7/2009 | Lu |
| 7,575,896 B2 | 8/2009 | Yu |
| 7,579,515 B2 | 8/2009 | Miller |
| 7,582,301 B1 | 9/2009 | Bridon |
| 7,608,271 B2 | 10/2009 | Bridon |
| 7,638,608 B2 | 12/2009 | Kapteyn |
| 7,645,865 B2 | 1/2010 | Russell |
| 7,655,393 B2 | 2/2010 | Hasumi |
| 7,655,413 B2 | 2/2010 | Butt |
| 7,666,668 B2 | 2/2010 | Bujard |
| 7,666,868 B2 | 2/2010 | Maier |
| 7,671,253 B2 | 3/2010 | Fabijanski |
| 7,687,611 B2 | 3/2010 | Kapteyn |
| 7,704,969 B2 | 4/2010 | Hart |
| 7,709,621 B2 | 5/2010 | Kinoh |
| 7,727,538 B2 | 6/2010 | Quinn |
| 7,741,431 B2 | 6/2010 | Allon |
| 7,741,453 B2 | 6/2010 | Erickson |
| 7,744,896 B1 | 6/2010 | Ensoli |
| 7,750,134 B2 | 7/2010 | Godzik |
| 7,795,380 B2 | 9/2010 | Rice |
| 7,803,617 B2 | 9/2010 | Hammerschmidt |
| 7,807,363 B2 | 10/2010 | Wang |
| 7,811,803 B2 | 10/2010 | Madura |
| 7,820,624 B2 | 10/2010 | Hart |

(56) References Cited

U.S. PATENT DOCUMENTS

| | | |
|---|---|---|
| 7,829,104 B2 | 11/2010 | Sun |
| 7,829,290 B2 | 11/2010 | Fang |
| 7,838,637 B2 | 11/2010 | Kontermann |
| 7,842,460 B2 | 11/2010 | Butt |
| 7,879,813 B2 | 2/2011 | Chatterton |
| 7,881,468 B2 | 2/2011 | Haddad |
| 7,910,364 B2 | 3/2011 | Lima |
| 7,919,075 B1 | 4/2011 | Michal |
| 7,964,571 B2 | 6/2011 | Fewell |
| 7,973,019 B1 | 7/2011 | Chatterton |
| 7,981,669 B2 | 7/2011 | Coffin |
| 7,982,022 B2 | 7/2011 | Russell |
| 7,989,185 B2 | 8/2011 | Pourmand |
| 7,993,656 B2 | 8/2011 | Steward |
| 7,993,826 B2 | 8/2011 | Giesing |
| 7,999,073 B2 | 8/2011 | Schmidt |
| 8,007,786 B2 | 8/2011 | Mancini |
| 8,034,910 B2 | 10/2011 | Wang |
| 8,039,587 B2 | 10/2011 | Khan |
| 8,052,979 B2 | 11/2011 | Steward |
| 8,053,552 B2 | 11/2011 | VonKnebel-Doeberitz |
| 8,062,891 B2 | 11/2011 | Khan |
| 8,071,110 B2 | 12/2011 | Steward |
| 8,088,747 B2 | 1/2012 | Benvegnu |
| 8,103,278 B2 | 1/2012 | Tsao |
| 8,110,545 B2 | 2/2012 | Nieva Escandon |
| 8,114,581 B2 | 2/2012 | Chien |
| 8,124,843 B2 | 2/2012 | Fabijanski |
| 8,133,733 B2 | 3/2012 | Khan |
| 2002/0031818 A1 | 3/2002 | Ronai |
| 2002/0086356 A1 | 7/2002 | Tuschl |
| 2002/0127692 A1 | 9/2002 | Ink |
| 2002/0132990 A1 | 9/2002 | Huston |
| 2002/0151028 A1 | 10/2002 | Lima |
| 2002/0152487 A1 | 10/2002 | Bujard |
| 2002/0152489 A1 | 10/2002 | Bujard |
| 2002/0155095 A1 | 10/2002 | Nagabhushan |
| 2003/0022315 A1 | 1/2003 | Bujard |
| 2003/0049842 A1 | 3/2003 | Baron |
| 2003/0054000 A1 | 3/2003 | Dowdy |
| 2003/0104622 A1 | 6/2003 | Robbins |
| 2003/0186233 A1 | 10/2003 | Chesnut |
| 2003/0186281 A1 | 10/2003 | Hillen |
| 2003/0237112 A1 | 12/2003 | Brown |
| 2004/0003417 A1 | 1/2004 | Bujard |
| 2004/0009922 A1 | 1/2004 | Mochly-Rosen |
| 2004/0072739 A1 | 4/2004 | Anderson |
| 2004/0091878 A1 | 5/2004 | Sera |
| 2004/0101874 A1 | 5/2004 | Ghosh |
| 2004/0176282 A1 | 9/2004 | Dalby |
| 2004/0180423 A1 | 9/2004 | Studier |
| 2005/0015830 A1 | 1/2005 | Dorokhov |
| 2005/0037335 A1 | 2/2005 | Hillen |
| 2005/0042603 A1 | 2/2005 | Wang |
| 2005/0147993 A1 | 7/2005 | Khan |
| 2005/0154188 A1 | 7/2005 | Kim |
| 2005/0169904 A1 | 8/2005 | Payne |
| 2006/0211647 A1 | 9/2006 | Khan |
| 2006/0222657 A1 | 10/2006 | Dowdy |
| 2007/0037246 A1 | 2/2007 | Butt |
| 2007/0196334 A1 | 8/2007 | Khan |
| 2007/0212782 A1 | 9/2007 | Studier |
| 2007/0224682 A1 | 9/2007 | Studier |
| 2007/0259414 A1 | 11/2007 | Butt |
| 2008/0222750 A1 | 9/2008 | Khan |
| 2009/0093026 A1 | 4/2009 | Dowdy |
| 2009/0123468 A1 | 5/2009 | Khan |
| 2009/0208478 A1 | 8/2009 | Khan |
| 2009/0215895 A1 | 8/2009 | Ferrante |
| 2009/0227655 A1 | 9/2009 | Khan |
| 2009/0280531 A1 | 11/2009 | Wang |
| 2010/0021987 A1 | 1/2010 | Zuo |
| 2010/0040649 A1 | 2/2010 | Berkhout |
| 2010/0048480 A1 | 2/2010 | Bommarius |
| 2010/0112658 A1 | 5/2010 | Hughes |
| 2011/0055976 A1 | 3/2011 | Kandzia |
| 2011/0143362 A1 | 6/2011 | Oyler |
| 2011/0247088 A1 | 10/2011 | Bujard |
| 2011/0300600 A1 | 12/2011 | Khan |
| 2011/0319193 A1 | 12/2011 | Isogawa |
| 2012/0005776 A1 | 1/2012 | Khan |
| 2012/0009625 A1 | 1/2012 | Qiao |
| 2012/0149097 A1 | 6/2012 | Khan |

FOREIGN PATENT DOCUMENTS

| | | |
|---|---|---|
| KR | 20030012226 | 2/2003 |
| WO | 9727742 | 8/1997 |
| WO | 9846271 | 10/1998 |
| WO | 0019993 | 4/2000 |
| WO | 0012732 | 9/2000 |
| WO | 0058488 | 12/2000 |
| WO | 0175164 | 10/2001 |
| WO | 03025195 | 3/2003 |
| WO | 03052067 | 6/2003 |
| WO | 03076561 | 9/2003 |
| WO | 03087162 | 10/2003 |
| WO | 03087768 | 10/2003 |
| WO | 2004061456 | 7/2004 |
| WO | 2005003766 | 1/2005 |
| WO | 2005056752 | 6/2005 |
| WO | 2008072781 | 6/2008 |

OTHER PUBLICATIONS

Anziano and Butow, 'Splicing-defective mutants of the yeast mitochondrial COXI gene can be corrected by transformation with a hybrid maturase gene' Proc. Netl. Acad. Sci. U.S.A., 88(13):5592-6 (1991).

Barka, et al., "Transduction of TAT-HA-beta-galactosidase fusion protein into salivary gland-derived cells and organ cultures of the developing gland, and into rat submandibular gland in vivo", J Histochem Cytochem, 48(11):1453-60 (2000).

Bayona-Bafaluy, 'Rapid directional shift of mitochondrial DNA heteroplasmy in animal tissues by a mitochondrially targeted restriction endonuclease,'Proc. Nat!, Acad. Sci, U S A. 102(40):14392-7(2005).

Bennett, et al., "Mitochondrial gene therapy increases respiration and election transport chain expression in a mitochondrial DNA-based cell model of sporadic Parkinson\s disease", Annual meeting of the Society for Neuroscience (SFN) (2008).

Bhat and Epelboym, 'Quantitative analysis of total mitochondrial DNA: competitive polymerase chain reaction versus real-time polymerase chain reaction', J. Biochem. Mol. Toxicol., 18(4):180-6 (2004).

Blanchi, "Prokaryotic HU and eukaryotic HMG1: a kinked relationship", Molecular Microbiology, 14(1):1-5 1994.

Brydges, et al., "Mutation of an unusual mitochondrial targeting sequence of SODB2 produces multiple targeting fates in toxoplasma gondii", J Cell Sci., 116 (22):4675-86 (2003).

Bustin, et al., 'Recombinant human chromosomal proteins HMG-14 and HMG-17', Nucleic Acids Res., 19(11):3115-21(1991).

Carillo and Lipman, "The Multiple Sequence Alignment Problem in Biology", SIAM J Applied Math., 48:1073 (1988).

Carrozzo, et al., 'Maternally-inherited Leigh syndrome-related mutations bolster mitochondrial-mediated apoptosis', J. Neurochem., 90(2):490-501 (2004).

Cervin, et al., 'Cosegregation of MIDD and MODY in a pedigree: functional and clinical consequences', Diabetes, 53(71:1894-9 (2004).

Chang, et al., "Cellular internalization of fluorescent proteins via arginine-rich intracellular delivery peptide in plant cells", Plant Cell Physiol., 46(3):482-488 (2005).

Chen, et al., 'Determination of normal ranges of mitothondrial respiratory activities by mtDNA transfer from 54 Human subjects to mtDNA-less HeLa cells for identification of the pathogenicities of mutated mtDNAs', J. Biochem (Tokyo), 135(2):237-43 (2004).

Chen, et al., "A polar octapeptide fused to the N-terminal fusion peptide solublizes the influenza virus HA2 subunit ectodomain", Biochem, 37(39):13643-9 (1998) Abstract only.

(56) References Cited

OTHER PUBLICATIONS

Chinnery, at at., 'Peptide nucleic acid delivery to human mitochondria', Gene Thu., 6(12):1919#2D(s#(1999).
Claros and Vincens, 'Computational method to predict mitochondrially imported proteins and their targeting sequences', fur. J. Biochem., 241(3):779-86 (1996).
Cline and Henry 'Import and routing of nucleus-encoded chloroplast proteins', Anna. Rev. Cell Dev. Biol., 12:1-26 (1996).
D'Souza, et al., 'DQAsome-mediated delivery of plasmid DNA toward mitochondria in living cells', J.Contro/. Release, 92(1-2):189-97 (2003).
D'Souza 'Gene therapy of the other genome: the challenges of treating mitochondrial DNA defects' Pharm Res. 24(2):228-38(2007).
Dairaghi, et al., "Addition of a 29 residue carboxyl-terminal tail converts a simple HMG box-containing protein into a transcriptional activator", J Mol. Biol., 249:11-28 (1995).
Del Gaizo, 'A novel TAT-mitochondrial signal sequence fusion protein is processed, stays in mitochondria, and crosses the placenta,'Mot. Ther, 7 (6):720-30(2003).
Dement, et al., 'Dynamic mitochondrial localization of nuclear transcription factor HMGA1', Exp Cell Res. 307(2):388-401 (2005).
Derossi, at al., 'The third helix of the Antennapedia homeodomain translocates through biological membranes', J. Rio!. Dem., 269(14):10444-50 (1994).
Dietz and Schooner, "Advances in Phytoremediation", Enviro. Health Petspectives, 109(Supp 1):163-18 (2001).
Dolgilevich, et al., "Transduction of TAT fusion proteins into osteoclasts and osteoblasts", Biochem Biophy Res Comm, 298(3):505-9 (2002) Abstract only.
Emanuelsson, et al., 'Predicting subcellular localization of proteins based on their N-terminal amino acid sequence', J. Mol. Biol., 300(4):1005-16 (2000).
Falkenberg, et al., 'Mitochondrial transcription factors B1 and B2 activate transcription of human mtDNA', Nat. Genet., 31(3):289-94 (2002).
Fischer, et al., 'Cellular delivery of impermeable effector molecules in the form of conjugates with peptides capable of mediating membrane translocation', Bioconjug. Chem., 12(6):825-41 (2001).
Fisher, et al., 'Promoter selection in human mitochondria involves binding of a transcription factor to orientation independent upstream regulatory elements', Cell, 50(2):247-58 (1987).
Flierl, et at., 'Targeted delivery of DNA to the mitochondria! compartment via import sequence-conjugated peptide nucleic acid', Mol. Ther., 7(4):550-7 (2003).
Fortunati et al, A multi-domain protein for b1 integrin-targeted DNA delivery, Gene Therapy (2000) 7, 1505-1515 (2000).
Frankel and Pabo, 'Cellular uptake of the tat protein from human immunodeficiency virus', Cell, 55(6):1189-93 (1988).
Futaki et al, Arginine-rich Peptides, The Journal of Biological Chemistry vol. 276, No. 8, Issue of Feb. 23, pp. 5836-5840,2001.
GenBank, 'Accession No. AF151833' (PRI May 18, 2000, direct submission May 17, 1999).
GenBank, 'Accession No. AK026835' (PRI Sep. 12, 2006, direct submission August#s)2C# 2000).
Genbank, Accession No. NM 003201, "*Homo sapiens* transcription factor A, mitochondrial (TFAM), nuclear gene encoding mitochondrial protein, mRNA", 4 pages, First available Mar. 24, 1999, accessed Sep. 8, 2009.
Glover and Lindsay, "Targeting proteins to mitochondria: a current overview", Biochem. J., 284:609-20 (1992).
Grosschedl, et al., "HMG domain proteins: architectural elements in the assembly of nucleoprotein structures", Trends Genet., 10(3):94-100 (1994).
Guo, et al., "TAT-mediated protein transduction into human corneal epithelial cells: p15 (INK4b) inhibits cell proliferation and stimulates cell migration", Invest Ophthalmology, 45 (6):1804-11 (2004).
Guy, et al., 'Rescue of a mitochondrial deficiency causing Leber Hereditary Optic Neuropathy', Ann. Neurol., 52(5):534-42 (2002).

Hayashi, et al., "Reverse of age-dependent memory impairment and mitochondrial DNA damage in microglia by an overexpression of human mitochondrial transcription factor A in mice", J. Neurosci., 28(34):8624-34 (2008).
Ho, et al., 'Synthetic protein transduction domains: enhanced transduction potential in vitro and in vivo', Cancer Res., 61(2):474-7 (2001).
Hokari, et al., "Overexpression of mitochondrial transcription factor A (TFAM) ameliorates delayed neuronal death due to transient forebrain ischemia in mice", Neuropathology, 30 (4):401-7 (2010).
Ignatovich, et al., 'Complexes of plasmid DNA with basic domain 47.57 of the HIV-1 Tat protein are transferred to mammalian cells by endocytosis-mediated pathways', J. Biol.. Chem., 278(43):42625-36 (2003).
Ikeuchi, et al., "Overexpression of mitochondrial transcription factor A ameliorates mitochondrial deficiencies and cardiac failure after myocardial infarction", Circulation, 112:683-90 (2005).
Iyer, et al., "Recombinant mitochondrial transcription factor A with N-terminal mitochondrial transduction domain increases respiration and mitochondrial gene expression in G11778A Leber's hereditary optic neuropathy cybrid cells", Nature Proceedings, hdl:10101/npre.2008.2084.1 (2008).
Iyer, et al., "Mitochondrial gene replacement in human pluripotent stem cell-derived neural progenitors", Gene Therapy, 19(5):469-75 (2012).
Iyer, et al., "Protein-medicated mtDNA transfection (Protofection®) increases respiration and mitochondrial DNA gene copy numbers and expression in G11778A LHON cybrids", Setting the Pace in Mitochondrial Medicine, United Mitochondrial Disease Foundation (Contribute Talk) (2008).
Iyer, et al., "Towards a mitochondrial gene therapy of human genetic diseases", Annual meeting of the Society for Neuroscience (SFN) (2008), p. 1-4.
Iyer, "Development of mitochondrial gene therapy for neurodegenerative diseases of children and adults", (Invitation). Annual Meeting of the American Neurological Assoc., (2009). (Contributed Talk). (Information for the public was provided at http://www.ptproductsonline.com/reuters_article.asp?id=20091016scie004.html), p. 1-4.
Iyer, "Mitochondrial genome manipulation to study human neurodegenerative disorders", (Invitation), International Course on High-resolution Respirometry, Schroken, Austria. (Contributed Talk) (2009).
Iyer, "Protein-Medicated transfection increases respiration and mitochondrial gene expression in G11778A LHON cybrid cells", (Invitation) Host: Dr. David Clayton, Howard Hughes Medical Institute, Janelia Farm Research Campus, (Contributed Talk) (2008).
Jacobs, et al, Making mitochondrial mutants, TRENDS in Genetics vol. 17 No. 11 Nov. 2001.
Kabouridis, 'Biological applications of protein transduction technology', Trends BiatechnoL, 21(11):498-503 (2003).
Kanki, et al., "Architectural role of mitochondrial transcription factor A in maintenance of human mitochondrial DNA," Mol. Cell. Biol., 24(22): 9823-9834 (2004).
Kaufman et al., "The mitochondrial transcription factor TFAM coordinates the assembly of multiple DNA molecules into nucleoid-like structure", FEBS J, 274:6488-99 (2007).
Keeney, et al., "Mitochondrial gene therapy augments mitochondrial physiology in a Parkinson\s disease cell model", Human Gene Therapy, 20:897-907 (2009).
Khadake and Rao, 'Condensation of DNA and chromatin by an SPKK—containing octapeptide repeat motif present in the C-terminus of histone H1', Biochemistry, 36(5):1041-51 (1997).
Khan, 'Development of mitochondria' gene replacement therapy,' J. Bioenergetics and Biomembranes 36L387-393(2004).
Khan, et al., "Cell and animal models of mtDNA biology: progress and prospects", Am J Physical Cell Physiol, 292:C658-69 (2007).
Khan, "Mitochondrial gene therapy for neurologic disease", Graduate Dissertation to the Graduate Faculty of the Uni. of Virginia., presented Dec. (2005).

(56) References Cited

OTHER PUBLICATIONS

Krueger, et al, Peripheral-type benzodiazepine receptors mediate translocation of cholesterol from outer to inner mitochondrial membranes in adrenocortical cells, J. Biol. Chem., vol. 265, Issue 25, 15015-15022, Sep. 1990.
Laudet, et al., "Ancestry and diversity of the HMG box superfamily", Nuc. Acids Res., 21(10):2493-2501 (1993).
Lebedeva and Stein, "Antisense Oligonucleotides: Promise and Reality", Annu. Rev. Pharmacol. Toxicol., 41:403-19 (2001).
Lee, et al., "Identification of a signal that distinguishes between the chloroplast outer envelope membrane and the endomembrane system in vivo", Plant Cell, 13 (10):2175-90 (2001).
Levy, et al., "Cytoplasmic transfer in oocytes: biochemical aspects", Hum. Reprod. Update, 10(3):241-50 (2004).
Liu, et al., 'Mitochondria! DNA mutation and depletion increase the susceptibility of human cells to apoptosis', Ann. N.Y. Acad. Sci, 1011:133-45 (2004).
Lu and Hansen, 'Revisiting the structure and functions of the linker histone C-terminal tail domain', Biochem. Cell Biol., 81(3):173-6 (2003).
Luo and Saltzman, 'Synthetic DNA delivery systems', Nat. Biotechnol., 18 (1):33-7 (2000).
Mahata, "Functional delivery of a cytosolic tRNA into mutant mitochondria of human cells", Science, 314:471-74 (2006).
Maliga, 'Plant Biotechnology 2007: all three genomes make contributions to progress' Current Opinion in Biotech. 18:97-99(2007).
Mastrobattista, et al., "Functional characterization of an endosome-disruptive peptide and its application in cytosolic delivery of immunoliposome-entrapped proteins", J Biol. Chem., 277(30):27135-43 (2002).
Matsushima, et al., "Functional domains of chicken mitochondrial transcription factor A for the maintenance of mitochondrial DNA copy number in lymphoma cell line DT40", J. Biol. Chem., 278(33):31149-58 (2003).
Matsushita, et al., "A high-efficiency protein transduction system demonstrating the role of PKA in long-lasting long term potentiation", J. Neurosci., 21(16):6000-07 (2001).
McCulloch, et al., "Human mitochondrial transcription factor B1 interacts with the C-terminal activation region of h-mtTFA and stimulates transcription independently of its RNA methyltransferase activity", Molecular and Cellular Biology, 23(16):5816-24 (2003).
Michiue, et al., "The NH2 terminus of influenza virus hemagglutinin-2 subunit peptides enhances the antitumor potency of polyarginine-mediated p53 protein transduction", J Biol. Chem., 280(9):8285-9 (2005).
Mistry, et al., 'Recombinant HMG1 protein produced in *Pichia pastor's*: a nonviral gene delivery agent', Biotechniques, 22(4):718#2D)s#(1997).
Muratovska, at A, 'Targeting peptide nucleic acid (PNA) oligomers to mitochondria within cells by conjugation to lipophilic cations: implications for mitochondrial DNA replication, expression and disease', Nucleic Acids Res., 29(9):1852-63 (2001).
Murphy, 'Selective Targeting of Bioactive Compounds to Mitochondria,' Trends in Biotech, 15(8):326-30(1997).
Nagahara, et al., "Transduction of full-length TAT fusion proteins into mammalian cells: TAT-p27Kip1 induces cell migration", Nat. Med., 4(12):1449-52 (1998).
Neupert, 'Protein import into mitochondria', Annu. Rev. Biochem., 66:863-917 (1997).
Nishiyama, et al., "Over-expression of Tfam improves the mitochondrial disease phenotypes in a mouse model system", Biochem Biophy Res Comm., 401:26-31 (2010).
Noguchi et al, Protein transduction technology offers a novel therapeutic approach for diabetes, J Hepatobiliary Pancreat Surg (2006) 13:306-313.
Oca-Cossio, et al., 'Limitations of allotopic expression of mitochondrial genes in mammalian cells', Genetics, 165(2):707-20 (2003).
Opalanska, et al., 'Nucleic-acid therapeutics: basic principles and recent applications', Nat. Rev. Drug. Dis., 1:503-514 (2002).

Pastukh, et al., "Human mitochondrial transcription factor A possesses multiple subcellular targeting signals", Molecular Biol. Cell, 18:3225-36 (2007).
Petros, et at., 'mtDNA mutations increase tumorigenicity in prostate cancer', Prac. Natl. Acad. Sci. U.S.A., 102(3):719-24 (2005).
Pineau, et at., 'Targeting the NAD7 subunit to mitochondria restores a functional complex I and a wild type phenotype in the Icatiana sylvestris CMS II mutant lacking nad7', J. Biol. Chem., 280(28):25994-6001 (2005).
Porkka, et al., 'A fragment of the HMGN2 protein homes to the nuclei of tumor cells and tumor endothelial cells in vivo', Roc. Natl. Acad. Sci. USA, 99(11):7444-9 (2002).
Prosite Documentation PD0C00305, 'HMG boxes A and B and DNA-binding domains signature and profile', updated Dec. 2004.
Rantanen and Larsson, 'Regulation of mitochondrial DNA copy number during spermatogenesis', Hum. Reprod., 15 Suppl 2:86-91 (2000).
Rizzuto, et al., "Chimeric green fluorescent protein as a tool for visualizing subcellular organelles in living cells", Current Biology, 5(6):635-642 (1995).
Roberts, "Fast-track applications: The potential for direct delivery of proteins and nucleic acids to plant cells for the discovery of gene function", Plant Methods, 1:12 (2005).
Ross, et al., 'Cell-penetrating peptides do not cross mitochondrial membranes even when conjugated to a lipophilic catian: evidence against direct passage through phospholipid bilayers', Biochem. J., 383 (Pt. 3):457-68 (2004).
Ross and Murphy, 'Cell-penetrating peptides are excluded from the mitochondrial matrix', Biochem. Soc. Trans., 32(Pt 6):1072-4 (2004).
Rossignol, et al., 'Mitochondrial threshold effects', Biochem. J., 370(Pt 3):751-62 (2003).
Roubertoux, et al., 'Mitochondrial DNA modifies cognition in interaction with the nuclear genome and age in mice', Nat. Genet., 35(1):65-9 (2003).
Roucou, et al., 'Bioenergetic and structural consequences of allotopic expression of subunit 8 of yeast mitochondrial ATP synthase. The hydrophobic character of residues 23 and 24 is essential for maximal activity and structural stability of the enzyme complex', fur. J. Biochem., 261(2):444-51 (1999).
Russell, 'Replicating vectors for gene therapy of cancer: risks, limitations and prospects', Ear. J. Cancer, 30A(8):1165-1171 (1994).
Sandman, et at., 'Diversity of prokaryotic chromosomal proteins and the origin of the nucleosome', Cell. Mol. Life Sci., 54(12):1350-64 (1998).
Schaefer, et al., 'The epidemiology of mitochondrial disorders—past, present and future', Biochim. Biophys. Acta, 1659(2-3):115-20 (2004).
Schrank, 'Functional expression of the yeast Mn-superoxide dismutase gene in *Escherichia coli* requires deletion of the signal peptide sequence', Gene, 73 (1):121-30 (1988).
Seibel, 'Transfection of mitochondria: strategy towards a gene therapy of mitochondrial DNA diseases,' Nucleic Acids Res. 23(1):10-17 (1995).
Shore, 'Import and insertion of proteins into the mitochondrial outer membrane' Eur: J. Biochem. 227:9-18(1995).
Sloots, 'Recombinant derivatives of the human high-mobility group protein HMG82 mediate efficient nonviral gene delivery' FEBS 272:4221-4236(2005).
Smigrodzki and Khan, "Mitochondrial microheteroplasmy and a theory of aging and age-related disease", Rejuvenation. Res., 8(3):178-98 (2005).
Smith, at at., 'Delivery of bioactive molecules to mitochondria in viva', Proc. Natl. Acad. Sci U.S.A., 100(9):5407-12 (2003).
Srivastava, 'Manipulating mitochondrial DNA heteroplasmy by a mitochondrially targeted restriction endonuclease,' Hum. Mol. Genet,10 (26):3093-9(2001).
Stephens and Pepperkok, 'The many ways to cross the plasma membrane', Proc. Natl. Acad. Sci. U.S.A., 98(8):4295-8(2001).
Suarez, et al., Alterations in mitochondrial function and cytosolic calcium induced by hyperglycemia are restored by mitochondrial transcription factor A in cardiomyoctes', Am. J. Physiol. Cell Physiol., 295:01561.1568 (2008).

(56) References Cited

OTHER PUBLICATIONS

Subirana, 'Analysis of the charge distribution in the C-terminal region of histone H1 as related to its interaction with DNA', Biopolymers, 29(10-11):1351-7 (1990).

Suzuki, et al., "An NMR study on the DNA-binding SPKK motif and a model for its interaction with DNA", Protein Eng., 6(6):565-74 (1993).

Suzuki, et at., 'Maternal inheritance of diabetes is associated with inactive ALDH2 genotype in diabetics with renal failure in Japanese', Diabetes Res. Clin. Pract., 60(2):143-5 (2003).

Swerdlow, et al., "The Alzheimer\s disease mitochondrial cascade hypothesis", J Alzh. Dis., 20(suppl.2):265-79 (2010).

Swerdlow and Khan, "A mitochondrial cascade hypothesis for sporadic Alzheimer\s disease", Med. Hypotheses, 63:8-20 (2004).

Swerdlow and Khan, "The Alzheimer\s disease mitochondrial cascade hypothesis: an update", Exp Neurology, 218:308-15 (2009).

Tanaka, 'Gene therapy for mitochondrial disease by delivering restriction endonuclease Smal into mitochondria,' J. Sci. Biomed. 9(6 Pt 1):534-41(2002).

Taylor, et al., 'Mitochondrial DNA mutations in human colonic crypt stem cells', J. C/in. Invest., 112(9):1351-60 (2003).

Thomas, et al., "Recombinant human mitochondrial transcription factor A stimulates mitochondrial biogenesis and ATP synthesis, improves motor function after MPTP, reduces oxidative stress and increases survival after endotoxin ", Mitochondrion, 11:108-18 (2011).

Tiranti, et al., 'Identification of the gene encoding the human mitochondrial RNA polymerase (h-mtRPOL) by cyberscreening of the Expressed Sequence Tags database', Hum. Mol. Genet., 6(4):615-25 (1997).

Tiranti, et al., "Chromosomal localization of mitochondrial transcription factor A (TCF6), single-stranded DNA-binding protein (SSBP), and endonuclease G (ENDOG), three human housekeeping genes involved in mitochondrial biogenesis", Genomics, 25(2):559-64 (1995).vbTab.

Torchilin, et al., Peptide and protein drug delivery to and into tumors: challenges and solutions, DDT, 8(6):259-66 (2003).

Uherek & Wels, 'DNA-carrier proteins for targeted gene delivery', Adv. Drug Deliv. Rev. 44(2-3):153-66 (2000).

Vestweber, 'DNA-protein conjugates can enter mitochondria via the protein import pathway', Nature 338(6211):170-2(1989).

Wadia, et al., "Transducible TAT-HA fusogenic peptide enhances escape of TAT-fusion proteins after lipid raft macropinocytosis", Nature Med, 10(3):310-15 (2004).

Wagner, at al., 'Targeting of polyplexes: toward synthetic virus vector systems', Adv Gen, 53:333-354 (2005).

Wang, et al., 'Acquisition of double-stranded DNA-binding ability in a hybrid protein between *Escherichia coli* CspA and the cold shock domain of human YB-1 ', Mol. Microbiol. 38(3):526-34 (2000).

Weir, at al., 'Structure of the HMG box motif in the Bdomain of HMG1', EMBO J., 12(4):1311-9 (1993).

Weissig, 'Mitochondrial pharmaceutics', Mitachondrion, 3(4):229-44 (2004).

Wender, et al., 'The design, synthesis, and evaluation of molecules that enable or enhance cellular uptake: peptoid molecular transporters', Proc. Natl. Acad. Sci. U.S.A., 97 (24):13003-8 (2000).

Wharton, et al., "Membrane fusion by peptide analogues of influenza virus haemagglutinion" , J. Gen Virol., 69:1847-57 (1988).

Xin, et al., "DNA binding by single HMG box model proteins", Nucleic Acids Res., 28(20) 4044-50 (2000).

Zaitsev, et al., 'HI and HMG17 extracted from calf thymus nuclei are efficient DNA carriers in gene transfer', Gene ther. 4(6):586-92 (1997).

Zullo, et at., 'Stable transformation of CHO Cells and human NARP cybrids confers oligomycin resistance (oli(r)) following transfer of a mitochondrial DNA-encoded oli(r) ATPase6 gene to the nuclear genome: a model system for mtDNA gene therapy', Rejuvenation Res., 8(1):18#2D(s#(2005).

Charni, et al., "Oxidative phosphorylation induces de novo expression of MHC class I in tumor cells through the ERK5 pathway", J. Immun., 185:3498-3503 (2010).

Chen, "Mitohondrial membrane potential in living cells", Ann Rev Cell Devl. Biol., 4:155-81 (1988).

Favre, et al., "Mitochondrial pyrimidine nucleotide carrier (PNC1) regulates mitochondrial biogenesis and the invasive phenotype of cancer cells", Oncogene, 29:3964-76 (2010).

Schulz, et al., "Induction of oxidative metabolism by mitochondrial frataxin inhibits cancer growth", J Biol. Chem., 281(2):977-81 (2006).

Del Gaizo, et al., (2003) 'Targeting proteins to mitochondria using TAT', Molecular Genetics and Metabolism 80 pp. 170-180.

Genbank, Accession No. NM 005035, "*Homo sapiens* polymerase (RNA) mitochondrial (DNA directed) pseudogene 1 (POLRMTP1) on chromosome 17", 1 page, First available May 14, 1999, accessed Sep. 8, 2009.

Guo, et al., "Protein tolerance to random amino acid change", PNAS 101 (25):27-28 (2007).

Lesk, et al., "Prediction of Protein function from protein sequence and structure", Dept of Bio.and Mole. Bio. Monash Univ., pp. 27-28, downloaded Sep. 16, 2007.

Sandig, et al., "Direct gene transfer of HMG1 based DNA-protein complexes", J. Mol. Med., 73:B10 (1995) (Abstract).

Gross, et al., "BCL-2 family members and the mitochondria in apoptosis", Genes and Devel., 13:1899-1911 (1999).

Needleman and Wunsch, "A general method applicable to the search for similarities in the amino acid sequence of two proteins", J. Mol. Biol., 48:443-453 (1970).

Scarpulla, "Transcriptional paradigms in mammalian mitochondrial biogenesis and function," Physiol. Rev., 88: 611-638 (2008).

Matsui, et al., "Protein Therapy: in vivo protein transduction by polyarginine (11 R) PTD and subcellular targeting delivery," Curr. Protein. Pept. Sci., 4 (2):151-7 (2003).

Garstka, et al., "Import of mitochondrial transcription factor A (TFAM) into rat liver mitochondria stimulates transcription of mitochondrial DNA", Nucleic Acids Res., 1;31 (17):5039-47 (2003).

Genbank Accession No. AAA59849, "Mitochondria transcription factor 1 [*Homo sapiens*]", dated Jan. 10, 1995, accessed Apr. 5, 2013.

TRANSDUCIBLE POLYPEPTIDES FOR MODIFYING METABOLISM

CROSS-REFERENCE TO RELATED APPLICATIONS

This application is a continuation of U.S. Ser. No. 12/253,138 filed on Oct. 16, 2008; and is a continuation-in-part application of U.S. Ser. No. 13/399,434, filed Feb. 17, 2012, which is a continuation of U.S. Ser. No. 11/932,674 filed on Oct. 31, 2007, now U.S. Pat. No. 8,133,733; and is a continuation-in-part of U.S. Ser. No. 13/171,751, filed Jun. 29, 2011, now U.S. Pat. No. 8,470,929, which is a continuation of U.S. Ser. No. 11/930,892, filed on Oct. 31, 2007, now U.S. Pat. No. 8,062,891; and is a continuation-in-part of U.S. Ser. No. 11/389,432, filed on Mar. 24, 2006, now U.S. Pat. No. 8,507,277, which is a continuation-in-part of U.S. Ser. No. 10/972,963 filed on Oct. 25, 2004, now U.S. Pat. No. 8,039,587, which claims priority to U.S. Ser. No. 60/568,436 filed on May 5, 2004, and U.S. Ser. No. 60/513,983 filed on Oct. 24, 2003. Prior filed applications U.S. Ser. No. 12/253,138, U.S. Ser. No. 11/932,674, U.S. Ser. No. 11/930,892, U.S. Ser. No. 11/389,432, U.S. Ser. No. 10/972,963, U.S. Ser. No. 60/568,436, and U.S. Ser. No. 60/513,983 are each incorporated by reference herein in their entirety.

STATEMENT REGARDING FEDERALLY SPONSORED RESEARCH OR DEVELOPMENT

Aspects of the following disclosure were supported in part by grant number AG023443-02 awarded by the National Institutes of Health. Therefore, the United States has certain rights in the disclosure.

REFERENCE TO SEQUENCE LISTING

The Sequence Listing submitted Mar. 13, 2012, as a text file named "GNC0003CIP4CON_ST25.txt," created on Mar. 12, 2012, and having a size of 13,308 bytes is hereby incorporated by reference.

FIELD OF THE INVENTION

The present disclosure is generally directed to compositions and methods for the delivery of transducible DNA binding proteins to organelles, more particularly to compositions and methods for modifying mitochondria, for example inducing mitochondrial biogenesis and oxidative metabolism.

BACKGROUND

In the course of evolution, many organisms tackled the task of introducing macromolecules into living cells. Aside from the cell-specific, usually receptor-mediated or active uptake mechanisms, the general solution that has independently emerged in many lineages relies on peptides specifically evolved to interact with, and insert into lipid bilayer membranes. Thus, bacterial colicins, human porins, and protein transduction domains (PTDs) from diverse species share the motif of a positively charged alpha-helix, frequently with an amphipathic structure, which is capable of inserting into lipid membranes, and delivering larger cargoes intracellularly. Recent research reports confirm the successful use of PTDs fused to proteins for their delivery across biological boundaries, including the blood-brain barrier, and the placenta.

Mitochondria are the α-proteobacterial, energy producing and cell death controlling endosymbionts in all eukaryotic cells (Fitzpatrick, et al., *Mol Biol Eva*, 23(1):74-85 (2006)). The mitochondrial outer membrane has a lipid composition similar to that of eukaryotic plasma membranes, whereas the mitochondrial inner membrane contains a unique lipid, cardiolipin, and more closely resembles bacterial membranes. Mitochondria contain their own DNA, transcription and translation machinery, involved in producing proteins necessary to carry out oxidative phosphorylation. Many diseases are associated with a decline in mitochondrial number, mitochondrial function, or more specifically, oxidative phosphorylation. Furthermore, increasing mitochondrial function, number and/or oxidative phosphorylation in a basal or healthy state may increase the capabilities of cells and tissues heavily reliant on mitochondrial metabolism, such as brain and muscle.

Therefore it is an object of the invention to provide compositions and methods for increasing mitochondrial number, mitochondrial function and/or oxidative phosphorylation in a subject.

SUMMARY

Compositions and methods for increasing mitochondrial biological activity as well as numbers of mitochondria are provided. One embodiment provides modified polypeptides having a polynucleotide-binding domain, a targeting domain, for example an organelle specific targeting signal, and a protein transduction domain. In certain embodiments, the modified polypeptide has at least one HMG box domain, more typically at least two HMG box domains. The polypeptide is designed to enter cells and target specific organelles, such as mitochondria. The targeting signal helps direct the polypeptide to a site of interest, for example an organelle and thereby modify the function of the cellular organelle.

In a preferred embodiment, the recombinant polypeptide has at least 80, 85, 90, 95, 97, 99, or 100% sequence identity to

```
                                           (SEQ ID NO: 18)
MRRRRRRRRR RRGEGDIMGE WGNEIFGAIA GFLGGEMLSR

AVCGTSRQLP PVLGYLGSRQSSVLASCPKK PVSSYLRFSK

EQLPIFKAQN PDAKTTELIR RIAQRWRELP DSKKKIYQDA

YRAEWQVYKE EISRFKEQLT PSQIMSLEKE IMDKHLKRKA

MTKKKELTLL GKPKRPRSAYNVYVAERFQE AKGDSPQEKL

KTVKENWKNL SDSEKELYIQ HAKEDETRYH NEMKSWEEQM

IEVGRKDLLR RTIKKQRKYG AEEC
```

In another embodiment, the recombinant polypeptide is encoded by a nucleic acid having at least 80, 85, 90, 95, 97, 99, or 100% sequence identity to

```
                                           (SEQ ID NO: 19)
atgcggcgac gcagacgtcg tcgtcggcgg cgtcgcggcg agggtgatat tatgggtgaa tgggggaacg aaattttcgg agcgatcgct ggttttctcg gtggagaaat gttatcacgc
```

-continued

```
gcggtatgtg gcaccagcag gcagctgcct ccagtccttg gctatctggg ttcccgccag tcatcggtgt tagcatcatg tccgaaaaaa cctgtctcgt cgtacctgcg cttctccaaa gagcagctgc cgatttttaa agcgcaaaat ccggatgcta aaacgactga actgattcgc cgcattgcac aacgctggcg cgaactcccg gacagtaaaa aaaaaattta tcaggacgcc tatcgggctg aatggcaggt ctataaagag gagatctcac gcttcaaaga acaattaacc ccgagtcaaa taatgtctct ggaaaaagaa atcatggata aacacttaaa acgaaaggcg atgacgaaga aaaagaact gaccctgcta ggtaaaccta agcgtccgcg ctctgcgtat aatgtgtacg tggcagaacg ttttcaggag gccaaagggg attctccgca agaaaaactg aagaccgtca aagaaaattg gaaaaacctg tctgatagcg aaaaagaact gtacattcag cacgctaaag aagatgagac gcggtatcac aacgaaatga aatcttggga agagcagatg atcgaggtcg gtcggaagga tcttctccgt cgaaccatca aaaaacagcg taaatatgga gcagaagagt gaga
```

Another embodiment provides compositions and methods of inducing mitochondrial biogenesis and increasing mitochondrial oxidative metabolism by administering an effective amount of a recombinant polypeptide having a polynucleotide-binding domain, a targeting domain, and a protein transduction domain to a cell to increase mitochondrial biogenesis relative to a control. One embodiment provides a pharmaceutical composition consisting essential of a recombinant polypeptide having a polynucleotide-binding domain, a targeting domain, and a protein transduction domain and a pharmaceutically acceptable carrier or excipient. Preferably the polynucleotide-binding domain includes TFAM or a fragment thereof capable of binding a polynucleotide. Another embodiment provides a method for reducing body weight by administering an effective amount of the disclosed polypeptides to a subject to increase mitochondrial oxidative metabolism in the subject.

A preferred embodiment provides a fusion protein having three polypeptide regions or domains. The first region is the N-terminus region and includes a PTD. The PTD is operably linked to the second region which includes a targeting signal or domain. The second region is operably linked to a third region including a polypeptide that binds to or condenses mitochondrial DNA. Preferably, the polynucleotide-binding polypeptide is a mitochondrial transcription factor. A preferred polypeptide that binds or condenses mitochondrial DNA includes, but is not limited to TFAM or a fragment thereof capable of binding or condensing mitochondrial DNA or of promoting or inducing transcription of mitochondrial DNA.

BRIEF DESCRIPTION OF THE DRAWINGS

FIG. 1A shows percent of control basal respiration versus days after treatment with recombinant TFAM. FIG. 1B shows percent of control mean mtDNA gene copy number versus days after treatment with recombinant TFAM. FIG. 1C shows percent of control mean mtRNA (cDNA) copy number.

DETAILED DESCRIPTION

1. Definitions

Figure 1A:
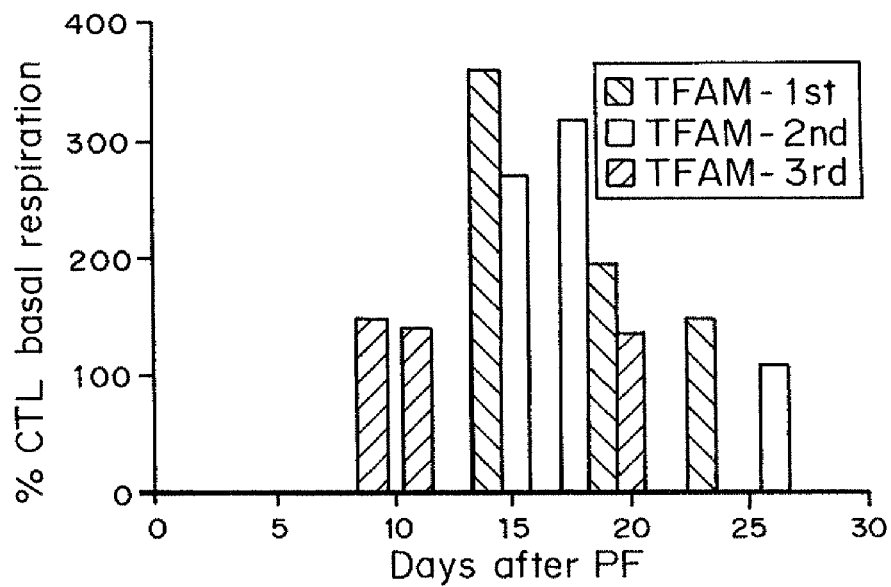
FIGS. 1A-C are bar graphs showing the effect of recombinant TFAM on basal respiration of LHON cybrid cells.

In describing and claiming the disclosed subject matter, the following terminology will be used in accordance with the definitions set forth below.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Praline (Pro, P), Serine (Ser, 5), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gin, His), (Asp: Glu, Cys, Ser), (Gin: Asn), (Gin: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptide as determined by the match between strings of such sequences. "Identity" and "similarity" can be readily calculated by known methods, including, but not limited to, those described in (Computational Molecular Biology, Lesk A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M, and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the *Needelman and Wunsch*, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the term "low stringency" refers to conditions that permit a polynucleotide or polypeptide to bind to another substance with little or no sequence specificity.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "treating" includes alleviating the symptoms associated with a specific disorder or condition and/or preventing or eliminating said symptoms.

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will assist the linked protein to be localized at the specific organelle.

"Localization Signal or Sequence or Domain" or "Targeting Signal or Sequence or Domain" are used interchangeably and refer to a signal that directs a molecule to a specific cell, tissue, organelle, intracellular region or cell state. The signal can be polynucleotide, polypeptide, or carbohydrate moiety or can be an organic or inorganic compound sufficient to direct an attached molecule to a desired location. Exemplary targeting signals include cell targeting signals known in the art such as those provided in Table 2 and described in Wagner et al., *Adv Gen,* 53:333-354 (2005) the disclosures of which are incorporated herein by reference in their entirety. It will be appreciated that the entire sequence listed in Table 2 need not be included, and modifications including truncations of these sequences are within the scope of the disclosure provided the sequences operate to direct a linked molecule to a specific cell type. Targeting signals of the present disclosure can have 80 to 100% sequence identity to the sequences in Table 2. One class of suitable targeting signals include those that do not interact with the targeted cell in a receptor:ligand mechanism. For example, targeting signals include signals having or conferring a net charge, for example a positive charge. Positively charged signals can be used to target negatively charged cell types such as neurons and muscle. Negatively charged signals can be used to target positively charged cells.

"Tropism" refers to the propensity of a molecule to be attracted to a specific cell, cell type or cell state. In the art, tropism can refer to the way in which different viruses and pathogens have evolved to preferentially target to specific host species, or specific cell types within those species. The propensity for a molecule to be attracted to a specific cell, cell type or cell state can be accomplished by means of a targeting signal.

"Cell Type" is a manner of grouping or classifying cells in the art. The term cell type refers to the grouping of cells based on their biological character determined in part through common biological function, location, morphology, structure, expression of polypeptides, nucleotides or metabolites.

"Cell State" refers to the condition of a cell type. Cells are dynamic throughout their life and can achieve various states of differentiation, function, morphology and structure. As used herein, cell state refers to a specific cell type throughout its lifetime.

As used herein, the term "cell surface marker" refers to any molecule such as moiety, peptide, protein, carbohydrate, nucleic acid, antibody, antigen, and/or metabolite presented on the surface or in the vicinity of a cell sufficient to identify the cell as unique in either type or state.

"Protein Transduction Domain" or PTD refers to a polypeptide, polynucleotide, carbohydrate, or organic or inorganic compounds that facilitates traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle. Exemplary PTDs include but are not limited to HIV TAT YGRKKRRQRRR (SEQ. ID NO. 1) or RKKRRQRRR (SEQ. ID NO. 2); 11 Arginine residues, or positively charged polypeptides or polynucleotides having 8-15 residues, preferably 9-11 residues.

2. Modified Polynucleotide Binding or Polynucleotide-Packaging Polypeptides

A. Polynucleotide Binding Domain

The compositions and methods for the delivery of a polypeptide, for example a DNA-binding protein, provided herein include polynucleotide-binding polypeptides or polynucleotide-packaging polypeptides optionally having a PTD and optionally having a targeting signal or domain. The modified or recombinant polypeptide can be any polypeptide known to bind or package a polynucleotide or a variant thereof. The recombinant polypeptide can be used as a therapeutic agent either alone or in combination with a polynucleotide. In one embodiment, the polynucleotide-binding polypeptide includes at least a portion of a member of the high mobility group (HMG) of proteins to bind a polynucleotide, in particular at least one HMG box domain.

Generally, the HMG domain includes a global fold of three helices stabilized in an 'L-shaped' configuration by two hydrophobic cores. The high mobility group chromosomal proteins HMG1 or HMG2, which are common to all eukaryotes, bind DNA in a non-sequence-specific fashion, for example to promote chromatin function and gene regulation. They can interact directly with nucleosomes and are believed to be modulators of chromatin structure. They are also important in activating a number of regulators of gene expression, including p53, Hox transcription factors and steroid hormone receptors, by increasing their affinity for DNA. HMG proteins include HMG-1/2, HMG-I(Y) and HMG-14/17.

The HMG-1/2-box proteins can be further distinguished into three subfamilies according to the number of HMG domains present in the protein, their specific of sequence recognition and their evolutionary relationship. The first group contains chromosomal proteins bound to DNA with no sequence specificity (class 1, HMG1 and HMG2), the second contains ribosomal and mitochondrial transcription factors which show sequence specificity in the presence of another associating factor when bound with DNA (class II, yeast ARS binding protein ABF-2, UBF and mitochondrial transcription factor mtTF-1), and the third contains gene-specific transcription factors which show sequence specific DNA binding (class III, lymphoid enhancer-binding factors LEF-1 and TCF-1; the mammalian sex-determining factor SRY, and the closely related SOX proteins; and the fungal regulatory proteins Mat-MC, Mat-a1, Ste11 and Rox1). The HMG1/2-box DNA binding domain is about 75 to about 80 amino acids and contains highly conserved proline, aromatic and basic residues. Common properties of HMG domain proteins include interaction with the minor groove of the DNA helix, binding to irregular DNA structure, and the capacity to modulate DNA structure by bending.

SOX (SRY-type HMG box) proteins have critical functions in a number of developmental processes, including sex determination, skeleton formation, pre-B and T cell development and neural induction. SOX9 plays a direct role during chondrogenesis by binding and activating the chondrocyte-specific enhancer of the Col2a1 gene. Loss of SOX9 gene function leads to the genetic condition known as Campomelic Dysplsia (CD), a form of dwarfism characterized by extreme skeletal malformation, and one in which three-quarters of XY individual are either intersexes or exhibit male to female sex reversal. There are more than 20 members cloned in SOX family. All of which contain an HMG domain, which can bind specifically to the double strand DNA motif and shares >50% identify with the HMG domain of SRY, the human testis-determining factor. The preferred DNA-binding site of SOX9 have been defined to be AGAACAATGG (SEQ ID NO: 3), which contains the SOX core-binding element (SCBE), AACAAT, flanking 5' AG and 3' GG nucleotides enhance binding by SOX9.

In one embodiment, the recombinant polynucleotide-binding protein has at least one HMG box domain, generally at least two, more particularly 2-5 HMG box domains. The HMG box domain can bind to an AT rich DNA sequence, for example, using a large surface on the concave face of the protein, to bind the minor groove of the DNA. This binding bends the DNA helix axis away from the site of contact. The first and second helices contact the DNA, their N-termini fitting into the minor groove whereas helix 3 is primarily exposed to solvent. Partial intercalation of aliphatic and aromatic residues in helix 2 occurs in the minor groove.

In other embodiments, the polynucleotide binding polypeptide can have at least one polynucleotide binding domain, typically two or more polynucleotide binding domains. The polynucleotide binding domains can be the same or different. For example, the polynucleotide-binding polypeptide can include at least on HMG box in combination with one or more DNA binding domains selected from the group consisting of an HMG box, homeodomain and POU domain; zinc finger domain such as $C_2H_2$ and $C_2C_2$; amphipathic helix domain such as leucine zipper and helix-loop-helix domains; and histone folds. The polynucleotide binding domain can be specific for a specific polynucleotide sequence, or preferably non-specifically binds to a polynucleotide. Alternatively, the polynucleotide-binding polypeptide can have more a combination of at least one polynucleotide binding domain that binds in a sequence specific manner and at least one polynucleotide binding-domain that binds DNA non-specifically.

Certain embodiments provide modified polynucleotide-binding polypeptides having a helix-turn-helix motif or at least a polynucleotide binding region of a helix-turn-helix protein. Helix-turn-helix proteins have a similar structure to bacterial regulatory proteins such as the 1 repressor and cro proteins, the lac repressor and so on which bind as dimers and their binding sites are palindromic. They contain 3 a helical regions separated by short turns which is why they are called helix-turn-helix proteins. One protein helix (helix 3) in each subunit of the dimer occupies the major groove of two successive turns of the DNA helix. Thus, in another embodiment, the disclosed polynucleotide-binding polypeptides can form dimers or other multi-component complexes, and have 1 to 3 helices.

In yet another embodiment, the modified polynucleotide-binding polypeptide includes a homeodomain or a portion of a homeodomain protein. Homeodomain proteins bind to a sequence of 180 base pairs initially identified in a group of genes called homeotic genes. Accordingly, the sequence was called the homeobox. The 180 bp corresponds to 60 amino acids in the corresponding protein. This protein domain is called the homeodomain. Homeodomain-containing proteins have since been identified in a wide range of organisms including vertebrates and plants. The homeodomain shows a high degree of sequence conservation. The homeodomain contains 4α helical regions. Helices II and III are connected by 3 amino acids comprising a turn. This region has a very similar structure to helices II and III of bacterial DNA binding proteins.

Yet another embodiment provides a modified polynucleotide-binding polypeptide having a zinc finger domain or at least a portion of a zinc finger protein. Zinc finger proteins have a domain with the general structure: Phe (sometimes Tyr)-Cys-2 to 4 amino acids-Cys 3 amino acids-Phe (sometimes Tyr)-5 amino acids-Leu-2 amino acids-His-3 amino acids-His. The phenylalanine or tyrosine residues which occur at invariant positions are required for DNA binding. Similar sequences have been found in a range of other DNA binding proteins though the number of fingers varies. For example, the SP1 transcription factor which binds to the GC box found in the promoter proximal region of a number of genes has 3 fingers. This type of zinc finger which has 2 cysteines and 2 histidines is called a $C_2H_2$ zinc finger.

Another type of zinc finger which binds zinc between 2 pairs of cysteines has been found in a range of DNA binding proteins. The general structure of this type of zinc finger is: Cys 2 amino acids-Cys-13 amino acids Cys-2 amino acids-Cys. This is called a $C_2C_2$ zinc finger. It is found in a group of proteins known as the steroid receptor superfamily, each of which has 2 $C_2C_2$ zinc fingers.

Another embodiment provides a modified polynucleotide-binding polypeptide having a leucine zipper or at least a portion of a leucine zipper protein. The first leucine zipper protein was identified from extracts of liver cells, and it was called C/EBP because it is an enhancer binding protein and it was originally thought to bind to the CAAT promoter proximal sequence. C/EBP will only bind to DNA as a dimer. The region of the protein where the two monomers join to make the dimer is called the dimerization domain. This lies towards the C-terminal end of the protein. When the amino acid sequence was examined it was found that a leucine residue occurs every seventh amino acid over a stretch of 35 amino acids. If this region were to form an a helix then all of these leucines would align on one face of the helix.

Because leucine has a hydrophobic side chain, one face of the helix is very hydrophobic. The opposite face has amino acids with charged side chains which are hydrophilic. The combination of hydrophobic and hydrophilic characteristics gives the molecule is amphipathic moniker. Adjacent to the leucine zipper region is a region of 20-30 amino acids which is rich in the basic (positively charged) amino acids lysine and arginine. This is the DNA binding domain—often referred to as the bZIP domain—the basic region of the leucine zipper. C/EBP is thought to bind to DNA by these bZIP regions wrapping round the DNA helix The leucine zipper-bZIP structure has been found in a range of other proteins including the products of the jun and fos oncogenes. Whereas C/EBP binds to DNA as a homodimer of identical subunits, fos cannot form homodimers at all and jun/jun homodimers tend to be unstable. However fos/jun heterodimers are much more stable. These fos/jun heterodimers correspond to a general transcription factor called API which binds to a variety of promoters and enhancers and activates transcription. The consensus API binding site is TGACTCA which is palindromic.

Another embodiment provides a modified polynucleotide-binding polypeptide having helix-loop-helix domain or a polynucleotide binding portion of a helix-loop-helix protein. Helix-loop-helix proteins are similar to leucine zippers in that they form dimers via amphipathic helices. They were first discovered as a class of proteins when a region of similarity was noticed between two enhancer binding proteins called E47 and E12. This conserved region has the potential to form two amphipathic separated by a loop hence helix-loop-helix. Next to the dimerization domain is a DNA binding domain, again rich in basic amino acids and referred to as the bHLH domain. These structures are also found in a number of genes required for development of the Drosophila nervous system—the Achaete-scute complex, and in a protein called MyoD which is required for mammalian muscle differentiation.

In still another embodiment, the modified polynucleotide binding polypeptide includes a histone polypeptide, a fragment of a histone polypeptide, or at least one histone fold. Histone folds exist in histone polypeptides monomers assembled into dimers. Histone polypeptides include H2A, H2B, H3, and H4 which can form heterodimers H2A-2B and H3-H4. It will be appreciated that histone-like polypeptides can also be used in the disclosed compositions and methods. Histone-like polypeptides include, but are not limited to, HMf or the histone from *Methanothermous fervidus*, other archaeal histones known in the art, and histone-fold containing polypeptides such as M71647, CBF, TAFII or transcription factor IID, SPT3, and Dr1-DRAP (Sanderman, K., et al., *Cell. Mol. Life Sci.* 54:1350-1364 (1998), which is incorporated by reference in its entirety).

One embodiment, among others, provides a non-histone polynucleotide-binding polypeptide, for example a polynucleotide-binding polypeptide comprising mitochondrial transcription factor A (TEAM) polypeptide, a variant thereof, or a fragment thereof sufficient to bind polynucleotides. Variant TFAM can have 80%, 85%, 90%, 95%, 99% or greater sequence identity with a reference TEAM, for example naturally occurring TFAM.

TEAM is a member of the high mobility group (HMG) of proteins having two HMG-box domains. TFAM as well as other HMG proteins bind, wrap, bend, and unwind DNA. Thus, embodiments of the present disclosure include polynucleotide binding polypeptides including one or more polynucleotide binding regions of the HMG family of proteins, and optionally induce a structural change in the polynucleotide when the polypeptide binds or becomes associated with the polynucleotide. By inducing a conformational change in the polynucleotide, the polypeptide packages the polynucleotide. It has been reported that TFAM binds to mitochondrial DNA in a ratio of 900:1 (Alam, T. I., et al., *Nucleic Acid Res.* 31(6):1640-1645 (2003)). It will be appreciated that the amount of polynucleotide-binding polypeptide used in the compositions and methods disclosed herein can vary depending on the size and amount of the polynucleotide to be delivered. Suitable ratios of polynucleotide-binding polypeptide to base pairs of polynucleotide to be delivered include, but are not limited to, about 1:1 to 1:1,000; more preferably 1:100; even more preferably 1: about 10 to about 20 base pairs of polynucleotide to be delivered. It will also be appreciated that TFAM, another polynucleotide-binding polypeptide, or a combination of two or more polynucleotide-binding polypeptides can be added to a polynucleotide to wrap or cover the polynucleotide, and thereby package the polynucleotide and protected it from degradation.

TFAM can be modified to include a PTD and optionally a targeting signal. The targeting signal can include a sequence of monomers that facilitates the localization of the molecule to a specific tissue, cell, or organelle. The monomers can be amino acids, nucleotide or nucleoside bases, or sugar groups such as glucose, galactose, and the like which form carbohydrate targeting signals.

B. Protein Transduction Domain

The polynucleotide-binding polypeptide can be modified to include a protein transduction domain (PTD), also known as cell penetrating peptides (CPPS). PTDs are known in the art, and include but are not limited to small regions of proteins that are able to cross a cell membrane in a receptor-independent mechanism (Kabouridis, P., *Trends in Biotechnology* (11):498-503 (2003)). Although several of PTDs have been documented, the two most commonly employed PTDs are derived from TAT (Frankel and Pabo, *Cell*, 55(6):1189-93 (1988)) protein of HIV and Antennapedia transcription factor from Drosophila, whose PTD is known as Penetratin (Derossi et al., *J Biol Chem.*, 269(14):10444-50 (1994)).

The Antennapedia homeodomain is 68 amino acid residues long and contains four alpha helices. Penetratin is an active domain of this protein which consists of a 16 amino acid sequence derived from the third helix of Antennapedia. TAT protein consists of 86 amino acids and is involved in the replication of HIV-1. The TAT PTD consists of an 11 amino acid sequence domain (residues 47 to 57; YGRKKRRQRRR (SEQ. ID. NO. 1)) of the parent protein that appears to be critical for uptake. Additionally, the basic domain Tat(49-57) or RKKRRQRRR (SEQ. ID NO. 2) has been shown to be a PTD. In the current literature TAT has been favored for fusion to proteins of interest for cellular import. Several modifications to TAT, including substitutions of Glutamine to Alanine, i.e., Q→A, have demonstrated an increase in cellular uptake anywhere from 90% (Wender et al., *Proc Natl Acad Sci USA.*, 97(24):13003-8 (2000)) to up to 33 fold in mammalian cells. (Ho et al., *Cancer Res.*, 61(2):474-7 (2001)) The most efficient uptake of modified proteins was revealed by mutagenesis experiments of TAT-PTD, showing that an 11 arginine stretch was several orders of magnitude more efficient as an intercellular delivery vehicle. Thus, some embodiments include PTDs that are cationic or amphipathic. Additionally exemplary PTDs include but are not limited to poly-Arg-RRRRRRR (SEQ. ID. NO.: 4); PTD-5 RRQRRTSKLMKR (SEQ. ID. NO.: 5); Transportan GWTLNSAGYLLGKINL-KALAALAKKIL (SEQ. ID. NO.: 6); KALA WEAK-LAKALAKALAKHLAKALAKALKCEA (SEQ. ID. NO.: 7); and RQIKIWFQNRRMKWKK (SEQ. ID. NO.: 8).

C. Targeting Signal or Domain

In still other embodiments, the modified polynucleotide-binding polypeptide is optionally modified to include a targeting signal or domain. The targeting signal or sequence can be specific for a host, tissue, organ, cell, organelle, non-nuclear organelle, or cellular compartment. For example, the compositions disclosed herein can be modified with galactosyl-terminating macromolecules to target the compositions to the liver or to liver cells. The modified compositions selectively enter hepatocytes after interaction of the carrier galactose residues with the asialoglycoprotein receptor present in large amounts and high affinity only on these cells. Moreover, the compositions disclosed here can be targeted to other specific intercellular regions, compartments, or cell types.

In one embodiment, the targeting signal binds to its ligand or receptor which is located on the surface of a target cell such as to bring the vector and cell membranes sufficiently close to each other to allow penetration of the vector into the cell. Additional embodiments of the present disclosure are directed to specifically delivering polynucleotides to specific tissue or cell types, wherein the polynucleotides can encode a polypeptide or interfere with the expression of a different polynucleotide. The polynucleotides delivered to the cell can encode polypeptides that can enhance or contribute to the functioning of the cell.

In a preferred embodiment, the targeting molecule is selected from the group consisting of an antibody or antigen binding fragment thereof, an antibody domain, an antigen, a T-cell receptor, a cell surface receptor, a cell surface adhesion molecule, a major histocompatibility locus protein, a viral envelope protein and a peptide selected by phage display that binds specifically to a defined cell.

Targeting polynucleotides to specific cells can be accomplished by modifying the disclosed compositions to express specific cell and tissue targeting signals. These sequences target specific cells and tissues, but in some embodiments the interaction of the targeting signal with the cell does not occur through a traditional receptor:ligand interaction. The eukaryotic cell comprises a number of distinct cell surface molecules. The structure and function of each molecule can be specific to the origin, expression, character and structure of the cell. Determining the unique cell surface complement of molecules of a specific cell type can be determined using techniques well known in the art.

One skilled in the art will appreciate that the tropism of the vector compositions described can be altered by merely changing the targeting signal. In one specific embodiment, compositions are provided that enable the addition of cell surface antigen specific antibodies to the vector for targeting the delivery of polynucleotides. Exemplary cell surface antigens are provided in Table 2 and described herein.

It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used a targeting moieties to target delivery to those cells which possess receptors for such hormones. Chemokines and cytokines can similarly be employed as targeting signals to target delivery of the complex to their target cells. A variety of technologies have been developed to identify genes that are preferentially expressed in certain cells or cell states and one of skill in the art can employ such technology to identify targeting signals which are preferentially or uniquely expressed on the target tissue of interest i. Brain Targeting In one embodiment, the targeting signal is directed to cells of the nervous system, including the brain and peripheral nervous system. Cells in the brain include several types and states and possess unique cell surface molecules specific for the type. Furthermore, cell types and states can be further characterized and grouped by the presentation of common cell surface molecules.

In one embodiment, the targeting signal is directed to specific neurotransmitter receptors expressed on the surface of cells of the nervous system. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter or ligand capable of specifically binding to a neurotransmitter receptor.

In one embodiment, the targeting signal is specific to cells of the nervous system which may include astrocytes, microglia, neurons, oligodendrites and Schwann cells. These cells can be further divided by their function, location, shape, neurotransmitter class and pathological state. Cells of the nervous system can also be identified by their state of differentiation, for example stem cells. Exemplary markers specific for these cell types and states are well known in the art and include, but are not limited to CD133 and Neurosphere.

ii. Muscle Targeting

In one embodiment, the targeting signal is directed to cells of the musculoskeletal system. Muscle cells include several types and possess unique cell surface molecules specific for the type and state. Furthermore, cell types and states can be further characterized and grouped by the presentation of common cell surface molecules.

In one embodiment, the targeting signal is directed to specific neurotransmitter receptors expressed on the surface of muscle cells. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter. Exemplary neurotransmitters expressed on muscle cells that can be targeted include but are not limited to acetycholine and norepinephrine, In one embodiment, the targeting signal is specific to muscle cells which consist of two major groupings, Type I and Type II. These cells can be further divided by their function, location, shape, myoglobin content and pathological state. Muscle cells can also be identified by their state of differentiation, for example muscle stem cells. Exemplary markers specific for these cell types and states are well known in the art include, but are not limited to MyoD, Pax7 and MR4.

iii. Tumor Targeting

In one embodiment, the targeting signal is used to selectively target tumor cells.

Tumor cells express cell surface markers which may only be expressed in the tumor or present in non tumor cells but preferentially presented in tumor cells. Exemplary tumor specific cell surface markers include, but are not limited to, alfa-fetoprotein (AFP), C-reactive protein (CRP), cancer antigen-50 (CA-50), cancer antigen-125 (CA-125) associated with ovarian cancer, cancer antigen 15-3 (CA15-3) associated with breast cancer, cancer antigen-19 (CA-19) and cancer antigen-242 associated with gastrointestinal cancers, carcinoembryonic antigen (CEA), carcinoma associated antigen (CAA), chromogranin A, epithelial mucin antigen (MC5), human epithelium specific antigen (HEA), Lewis(a) antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, and NCAM. In one embodiment, the targeting signal consists of antibodies which are specific to the tumor cell surface markers.

iv. Antibodies

Another embodiment provides an antibody or antigen binding fragment thereof bound to the disclosed recombinant polypeptides acting as the targeting signal. The antibodies or antigen binding fragment thereof are useful for directing the vector to a cell type or cell state. In one embodiment, the recombinant polypeptide possesses an antibody binding domain, for example from proteins known to bind antibodies such as Protein A and Protein G from Staphylococcus aureus. Other domains known to bind antibodies are known in the art and can be substituted. In certain embodiments, the antibody is polyclonal, monoclonal, linear, humanized, chimeric or a fragment thereof. Representative antibody fragments are those fragments that bind the antibody binding portion of the non-viral vector and include Fab, Fab', F(ab'), Fv diabodies, linear antibodies, single chain antibodies and bispecific antibodies known in the art.

In some embodiments, the targeting domain includes all or part of an antibody that directs the vector to the desired target cell type or cell state. Antibodies can be monoclonal or polyclonal, but are preferably monoclonal. For human gene therapy purposes, antibodies are derived from human genes and are specific for cell surface markers, and are produced to reduce potential immunogenicity to a human host as is known in the art. For example, transgenic mice which contain the entire human immunoglobulin gene cluster are capable of producing "human" antibodies can be utilized. In one embodiment, fragments of such human antibodies are employed as targeting signals. In a preferred embodiment, single chain antibodies modeled on human antibodies are prepared in prokaryotic culture.

Additional embodiments of the present disclosure are directed to specifically delivering the polypeptide to intracellular compartments or organelles. Eukaryotic cells contain membrane bound structures or organelles. Organelles can have single or multiple membranes and exist in both plant and animal cells. Depending on the function of the organelle, the organelle can consist of specific components such as proteins and cofactors. The polypeptides delivered to the organelle can enhance or contribute to the functioning of the organelle. Some organelles, such as mitochondria and chloroplasts, contain their own genome. Nucleic acids are replicated, transcribed, and translated within these organelles. Proteins are imported and metabolites are exported. Thus, there is an exchange of material across the membranes of organelles. In some embodiments, mitochondrial polypeptides are specifically delivered to mitochondria.

Exemplary organelles include the nucleus, mitochondrion, chloroplast, lysosome, peroxisome, Golgi, endoplasmic reticulum, and nucleolus. Synthetic organelles can be formed from lipids and can contain specific proteins within the lipid membranes. Additionally, the content of synthetic organdies can be manipulated to contain components for the translation of nucleic acids.

v. Nuclear Localization Signals

Compositions disclosed herein can include one or more nuclear localization signals. Nuclear localization signals (NLS) or domains are known in the art and include for example, SV 40 T antigen or a fragment thereof, such as PKKKRKV (SEQ. ID. NO.: 9). The NLS can be simple cationic sequences of about 4 to about 8 amino acids, or can be bipartite having two interdependent positively charged clusters separated by a mutation resistant linker region of about 10-12 amino acids. Additional representative NLS include but are not limited to GKKRSKV (SEQ. ID. NO.: 10); KSRKRKL (SEQ. ID. NO.: 11); KRPAATKK-AGQAKKKKLDK (SEQ. ID. NO.: 12); RKKRK-TEEESPLKDKAKKSK (SEQ. ID. NO.: 13); KDCVMNKHHRNRCQYCRLQR (SEQ. ID. NO.: 14); PAAKRVKLD (SEQ. ID. NO.: 15); and KKYENV-VIKRSPRKRGRPRK (SEQ. ID. NO.: 16).

vi. Mitochondria Targeting

In other embodiments of the present disclosure, modified polynucleotide-binding polypeptides are disclosed that specifically target mitochondria. Mitochondria contain the molecular machinery for the conversion of energy from the breakdown of glucose into adenosine triphosphate (ATP). The energy stored in the high energy phosphate bonds of ATP is then available to power cellular functions. Mitochondria are mostly protein, but some lipid, DNA and RNA are present. These generally spherical organdies have an outer membrane surrounding an inner membrane that folds (cristae) into a scaffolding for oxidative phosphorylation and electron transport enzymes. Most mitochondria have flat shelf-like cristae, but those in steroid secreting cells may have tubular cristae. The mitochondrial matrix contains the enzymes of the citric acid cycle, fatty acid oxidation and mitochondrial nucleic acids.

Mitochondrial DNA is double stranded and circular. Mitochondrial RNA comes in the three standard varieties; ribosomal, messenger and transfer, but each is specific to the mitochondria. Some protein synthesis occurs in the mitochondria on mitochondrial ribosomes that are different than cytoplasmic ribosomes. Other mitochondrial proteins are made on cytoplasmic ribosomes with a signal peptide that directs them to the mitochondria. The metabolic activity of the cell is related to the number of cristae and the number of mitochondria within a cell. Cells with high metabolic activity, such as heart muscle, have many well developed mitochondria. New mitochondria are formed from preexisting mitochondria when they grow and divide.

The inner membranes of mitochondria contain a family of proteins of related sequence and structure that transport various metabolites across the membrane. Their amino acid sequences have a tripartite structure, made up of three related sequences about 100 amino acids in length. The repeats of one carrier are related to those present in the others and several characteristic sequence features are conserved throughout the family.

Targeting of specific polypeptides to organelles can be accomplished by modifying the disclosed compositions to contain specific organelle targeting signals. These sequences target specific organelles, but in some embodiments the interaction of the targeting signal with the organelle does not occur through a traditional receptor:ligand interaction. The eukaryotic cell comprises a number of discrete membrane bound compartments, or organelles. The structure and function of each organelle is largely determined by its unique complement of constituent polypeptides. However, the vast majority of these polypeptides begin their synthesis in the cytoplasm. Thus organelle biogenesis and upkeep require that newly synthesized proteins can be accurately targeted to their appropriate compartment. This is often accomplished by amino-terminal signaling sequences, as well as post-translational modifications and secondary structure. For mitochondria, several amino-terminal targeting signals have been deduced and are known in the art.

In one embodiment, the organelle targeting signal can contain at least two, preferably 5-15, most preferably about 11 charged groups, causing the targeting signal to be drawn to organelles having a net opposite charge. In another embodiment, the targeting signal can contain a series of charged groups that cause the targeting signal to be transported into an organelle either against or down an electromagnetic potential gradient. Suitable charged groups are groups that are charged under intracellular conditions such as amino acids with charged functional groups, amino groups, nucleic acids, and the like. Mitochondrial localization/targeting signals generally consist of a leader sequence of highly positively charged amino acids. This allows the protein to be targeted to the highly negatively charged mitochondria. Unlike receptor:ligand approaches that rely upon stochastic Brownian motion for the ligand to approach the receptor, the mitochondrial localization signal of some embodiments is drawn to mitochondria because of charge.

In order to enter the mitochondria, a protein generally must interact with the mitochondrial import machinery, consisting of the Tim and Tom complexes (Translocase of the Inner/Outer Mitochondrial Membrane). With regard to the mitochondrial targeting signal, the positive charge draws the linked protein to the complexes and continues to draw the protein into the mitochondria. The Tim and Tom complexes allow the proteins to cross the membranes. Accordingly, one embodiment of the present disclosure delivers compositions of the present disclosure to the inner mitochondrial space utilizing a positively charged targeting signal and the mitochondrial import machinery. In another embodiment, PTD-linked polypeptides containing a mitochondrial localization signal do not seem to utilize the TOM/TIM complex for entry into the mitochondrial matrix, see Del Gaizo et al. *Mol Genet Metab.* 80(1-2):170-80 (2003).

Given the importance of mitochondria in human disease, cell proliferation, cell death, and aging, embodiments of the present disclosure also encompasses the manipulation of the mitochondrial function to supply the means by which known mitochondrial diseases (LHON, MELAS, etc.) and putative mitochondrial diseases (aging, Alzheimer's, Parkinson's, Diabetes, Heart Disease) can be treated.

Localization sequences suitable for use in the present disclosure are described in Emanuelson et al., Predicting Subcellular Localization of Proteins Based on Their N-terminal Amino Acid Sequence. *Journal of Molecular Biology.* 300 (4):1005-16, 2000 Jul. 21, and in Cline and Henry, Import and Routing of Nucleus-encoded Chloroplast Proteins. *Annual Review of Cell & Developmental Biology.* 12:1-26, 1996, the disclosures of which are incorporated herein by reference in their entirety. More particularly, proteins and genes that have mitochondria localization signals for targeting linked proteins or nucleic acids to the mitochondria are listed in TABLE 1. In one embodiment the mitochondria or chloroplast localization signal is operably linked to a virus surface protein. It will be appreciated that part or all of the sequences listed in Tables 1 can be used as organelle targeting signals.

TABLE 1

Localization Signals for Targeting to the Mitochondria. (verified using Mitochondrial Project MITOP Database -- http://mips.gsf.de/proj/medgen/mitop/)

| MITOP Designation (Accession No.) | Gene Name | Gene Name Full |
|---|---|---|
| 106092 (NP633590) | Etfa | electron transfer flavoprotein alpha chain precursor - mouse |
| 106098 (Q9DCW4) | Etfb | electron transfer flavoprotein beta chain - mouse |
| 107450 (NP000099) | Dld | dihydrolipoamide dehydrogenase precursor - human |
| 87979 (NP067274) | Ak3 | nucleoside-triphosphate--adenylate kinase 3 - mouse |
| 88529 (NP080720) | Cs | citrate synthase, mitochondrial |
| 891996 (AA031763) | Cps1 | carbamoyl-phosphate synthetase 1 |
| 97045 (NP032641) | Mod2 | malic enzyme complex, mitochondrial - mouse |
| 97499 (AAH49802) | Pcca | propionyl-CoA carboxylase alpha chain precursor - mouse |
| A27883 (NP000273) | PCCA | propionyl-CoA carboxylase alpha chain precursor |
| A28053 NP031647) | Cbr2 | carbonyl reductase (NADPH) - mouse |
| A29881 (XP331748) | mpp-2 | Mitochondrial processing peptidase beta subunit precursor (beta-mpp) (ubiquinol-cytochrome c reductase complexcore protein I) |
| A30605 (NP000008) | ACADS | acyl-CoA dehydrogenase precursor, short-chain-specific |
| A31998 (WP000117) | ETFA | electron transfer flavoprotein alpha chain precursor |
| A32422 | DBT | dihydrolipoamide S-(2-methyl-propanoyl)transferase precursor |
| A32800 (NP002147) | HSPD1 | heat shock protein 60 precursor |
| A36442 (XP326125) | mpp-1 | Mitochondrial processing peptidase alpha chain precursor |
| A37033 (NP002216) | IVD | isovaleryl-CoA dehydrogenase precursor |
| A37157 (NP898871) | BCKD | 3-methyl-2-oxobutanoate dehydrogenase (lipoamide) E1-beta chain precursor |
| A38234 | OGDH | oxoglutarate dehydrogenase (lipoamide) precursor |
| A39503 (NP002387) | ME2 | malate dehydrogenase (NAD+) precursor, mitochondrial |
| A40487 (NP004101) | FDXR | ferredoxin--NADP+ reductase, long form, precursor |
| A40559 (NP001599) | ACADL | long-chain-acyl-CoA dehydrogenase (LCAD) |
| A40872 | ALDH5 | aldehyde dehydrogenase (NAD+) 5 precursor, mitochondrial |
| A41581 (NP005720) | CYP3 | peptidylprolyl isomerase 3 precursor |
| A42224 (P22572) | arg-2 | Carbamoyl-phosphate synthase, arginine-specific, small chain precursor (arginine-specific carbamoyl-phosphate synthetase, glutamine chain) (cps-a) |
| A42845 | BDH | D-beta-hydroxybutyrate dehydrogenase precursor (3-hydroxybutyrate dehydrogenase) (fragment) |
| A45470 (AAP88794) | HMGC | hydroxymethylglutaryl-CoA lyase |
| A47255 (AAH55030) | Pcx | pyruvate carboxylase |
| A53020 (AAH53661) | PCCB | propionyl-CoA carboxylase beta chain precursor |
| A53719 (NP036216) | GLUDP | glutamate dehydrogenase (NAD(P)+) 2 precursor |
| A55075 (NP032329) | HspE1 | chaperonin-10 |
| A55680 (NP001600) | ACADS | short/branched chain acyl-CoA dehydrogenase precursor |
| A55723 (P42126) | DCI | dodecenoyl-CoA Delta-isomerase precursor, mitochondrial |
| A55724 (NP031408) | Acadm | Acyl-CoA dehydrogenase, medium-chain specific precursor (MCAD) |
| AA227572 (NM201263) | WARS2 | tryptophanyl-tRNA synthetase 2 (mitochondrial) - human |
| AB029948 (NP060297) | SerRS | mitochondrial seryl-tRNA synthetase (cDNA FLJ20450 FIS, CLONE KAT05607) - human |
| ACDL__MOUSE (AAH27412) | Acadl | Acyl-CoA dehydrogenase, long-chain specific precursor (LCAD) |
| AF047042 (AAC25560) | CS | citrate synthase, mitochondrial |
| AF097441 (NP006558) | FARS1 | phenylalanine-tRNA synthetase (FARS1) mRNA, nuclear gene encoding mitochondrial protein - human |
| ATPO__HUMAN (NP001688) | ATP5O | ATP synthase oligomycin sensitivity conferral protein precursor, mitochondrial |
| AXHU (AAP35327) | FDX1 | adrenodoxin precursor |
| CCHU (NP061820) | HCS | cytochrome c |
| CCNC (CAA29050) | cyc-1 | Cytochrome c |
| CE06620 (NP056155) | — | Probable leucyl-tRNA synthetase, mitochondrial |
| CE09597 (AAG31658) | — | Pyruvate dehydrogenase (E2) dihydrolipoamide acetyltransferase |
| CH10__MOUSE (NP032329) | Hspe1 | 10 KD heat shock protein, mitochondrial (hsp10) (10K chaperonin) mouse |
| CH60__CAEEL (NP497429) | hsp60 | Chaperonin homolog hsp60 precursor (heat shock protein 60) (hsp-60) |
| DEHUE2 (NP000681) | ALDH2 | aldehyde dehydrogenase (NAD+) 2 precursor, mitochondrial |
| DEHUE (NP005262) | GLUD1 | glutamate dehydrogenase (NAD(P)+) precursor |

TABLE 1-continued

Localization Signals for Targeting to the Mitochondria.
(verified using Mitochondrial Project MITOP Database
-- http://mips.gsf.de/proj/medgen/mitop/)

| MITOP Designation (Accession No.) | Gene Name | Gene Name Full |
|---|---|---|
| DEHULP (NP000099) | DLD | dihydrolipoamide dehydrogenase precursor |
| DEHUPA (NP000275) | PDHA1 | pyruvate dehydrogenase (lipoamide) alpha chain precursor |
| DEHUPB (AAH00439) | PDHB | pyruvate dehydrogenase (lipoamide) beta chain precursor |
| DEHUPT (NP005381) | PDHA2 | pyruvate dehydrogenase (lipoamide) alpha chain precursor, testis-specific (E1) |
| DEHUXA (NP000700) | BCKDH | 3-methyl-2-oxobutanoate dehydrogenase (lipoamide) alpha chain precursor |
| DEMSMM (P08249) | Mor1 | malate dehydrogenase precursor, mitochondrial |
| DSHUN | SOD2 | superoxide dismutase (Mn) precursor |
| ECHM_HUMAN (NP004083) | ECHS1 | enoyl-CoA hydratase, mitochondrial (short chain enoyl-CoA hydratase (SCEH)) |
| GABT_HUMAN (JC4022) | ABAT | 4-aminobutyrate aminotransferase, mitochondrial precursor (gamma-amino-N-butyrate-transaminase) (GABA transaminase) |
| GCDH_HUMAN (AAP35352) | GCDH | glutaryl-CoA dehydrogenase precursor (GCD) - human |
| GCDH_MOUSE (NP032123) | Gcdh | Glutaryl-CoA dehydrogenase precursor (GCD) - mouse |
| HCD1_CAEEL (NP499075) | — | Probable 3-hydroxyacyl-CoA dehydrogenase F54C8.1 |
| HCD2_CAEEL (NP509584) | — | Probable 3-hydroxyacyl-CoA dehydrogenase B0272.3 |
| HHMS60 (NP034607) | Hsp60 | heat shock protein 60 precursor |
| HMGL_MOUSE (AAB27965) | Hmgcl | hydroxymethylglutaryl-CoA lyase precursor (HG-CoA lyase) (HL) (3-hydroxy-3-methyl-glutarate-CoA lyase) |
| I48884 (AAC52130) | — | 2-oxoglutarate dehydrogenase E1 component (fragment) |
| I48966 (AAH05476) | Aldh2 | aldehyde dehydrogenase (NAD+) 2 precursor, mitochondrial |
| I49605 | Acads | Acyl-CoA dehydrogenase, short-chain specific precursor (SCAD) (butyryl-CoA dehydrogenase) |
| I52240 (NP000007) | ACAD | acyl-CoA dehydrogenase precurser, medium-chain-specific |
| I55465 (AAH39158) | PDK1 | pyruvate dehydrogenase kinase isoform 1 - human |
| I57023 (DSHUN) | Sod2 | superoxide dismutase (Mn) precursor |
| I70159 (AAC42010) | PDK2 | pyruvate dehydrogenase kinase isoform 2 - human |
| I70160 (NP005382) | PDK3 | pyruvate dehydrogenase kinase isoform 3 - human |
| JC2108 (AAA56664) | HADH | long-chain-fatty-acid beta-oxidation multienzyme complex alpha chain precursor, mitochondrial |
| JC2109 (NP000174) | HADH | long-chain-fatty-acid beta-oxidation multienzyme complex beta chain precursor, mitochondrial |
| JC2460 (AAH11617) | PC | pyruvate carboxylase precursor |
| JC4879 (NP005318) | SCHAD | 3-hydroxyacyl-CoA dehydrogenase, short chain-specific, precursor |
| KIHUA3 (AAH16180) | AK3 | nucleoside-triphosphate--adenylate kinase 3 |
| M2GD_HUMAN (AAF21941) | DMGD | dimethylglycine dehydrogenase, mitochondrial precursor (ME2GLYDH) - human |
| MDHM_HUMA (AAH01917) | MDH2 | malate dehydrogenase mitochondrial precursor (fragment) |
| O75439 | PMPC | mitochondrial processing peptidase beta subunit precursor (beta-MPP) (P-52) |
| ODO1_MOUSE (AAC52130) | Ogdh | 2-oxoglutarate dehydrogenase E1 component (alpha-ketoglutarate dehydrogenase) (fragment) |
| ODPA_CAEEL (NP495693) | — | Probable pyruvate dehydrogenase E1 component, alpha subunit precursor (PDHE1-a) |
| OWHU (NP000522) | OTC | ornithine carbamoyltransferase precursor |
| OWMS (CAA30121) | Otc | ornithine carbamoyltransferase precursor |
| P21549 (NP000021) | AGXT | alanine--glyoxylate aminotransferase |
| PUT2_HUMAN (NP733844) | ALDH4 | Delta-1-pyrroline-5-carboxylate dehydrogenase precursor (P5C dehydrogenase) |
| Q0140 (NP009320) | VAR1 | VAR1 - mitochondrial ribosomal protein |
| Q10713 (NP055975) | KIAA0123 | mitochondrial processing peptidase alpha subunit precursor (alpha-MPP) (P-55) (HA1523) |
| Q16654 (NP002603) | PDK4 | pyruvate dehydrogenase kinase isoform 4 - human |
| ROHU (CAA42060) | TST | thiosulfate sulfurtransferase |
| S01174 (NP034455) | Got2 | aspartate transaminase precursor, mitochondrial |
| S08680 (NP032676) | Mut | methylmalonyl-CoA mutase alpha chain precursor |
| S13025 (CAA39695) | nuo-40 | NADH dehydrogenase (ubiquinone) 40K chain |
| S13048 (PI9974) | cyt | cytochrome c |
| S16239 (AAH57347) | Glud | glutamate dehydrogenase (NAD(P)+) precursor |
| S23506 (NP032836) | Pdhal | pyruvate dehydrogenase (lipoamide) |
| S25665 (CAA32052) | DLAT_h | dihydrolipoamide S-acetyltransferase heart - human (fragment) |
| S26984 (P33540) | — | probable DNA-directed RNA polymerase - mitochondrion plasmid maranhar (SGC3) |
| S32482 (NP001976) | ETFB | electron transfer flavoprotein beta chain |
| S38770 (P42125) | Dci | 3,2-trans-enoyl-CoA isomerase, mitochondrial precursor (dodecenoyl-CoA delta-isomerase) |
| S39807 | Bckdhb | 3-methyl-2-oxobutanoate dehydrogenase (lipoamide) beta chain |
| S40622 (NP000246) | MUT | methylmalonyl-CoA mutase precursror (MCM) |
| S41006 (CAE65137) | — | hypothetical protein t05g5.6 |
| S41563 | cit-1 | citrate (si)-synthase, mitochondrial |
| S42366 | PRSS15 | Lon proteinase homolog |
| S42370 (NP499264) | — | citrate synthase homolog |
| S47532 (NP002148) | HSPE1 | heat shock protein 10 |
| S53351 (NP006671) | ME2.1 | malate dehydrogenase (oxaloacetate-decarboxylating) (NADP+) precursor, mitochondrial |
| S60028 (NP032023) | Fdxr | ferredoxin--NADP+ reductase precursor |
| S65760 (NP034152) | Dbt | dihydrolipoamide transacylase precursor |
| S71881 (NP031559) | Bckdha | branched chain alpha-ketoacid dehydrogenase chain E1-alpha precursor |
| SCOT_HUMA | OXCT | Succinyl-CoA: 3-ketoacid-coenzyme |

TABLE 1-continued

Localization Signals for Targeting to the Mitochondria.
(verified using Mitochondrial Project MITOP Database
-- http://mips.gsf.de/proj/medgen/mitop/)

| MITOP Designation (Accession No.) | Gene Name | Gene Name Full |
|---|---|---|
| (NP000427) | | A transferase precursor (succinyl CoA: 3-oxoacid CoA-transferase) (OXCT) |
| SODM_CAEEL (NP492290) | sod-2 | Superoxide dismutase precursor (Mn) |
| SODN_CAEEL (NP510764) | sod-3 | Superoxide dismutase precursor (Mn) |
| SYHUAE | ALAS2 | 5-aminolevulinate synthase 2 |
| SYHUAL (NP000679) | ALAS1 | 5-aminolevulinate synthase 1 precursor |
| SYLM_HUMAN (NP056155) | KIAA0028 | Probable leucyl-tRNA synthetase, mitochondrial precursor (Leucine--tRNA ligase) (Leurs) (KIAA0028) |
| SYMSAL | Alas2 | 5-aminolevulinate synthase mitochondrial precursor (erythroid-specific) (ALAS-E) |
| SYNCLM (XP323115) | leu-5 | leucine--tRNA ligase precursor, mitochondrial |
| SYNCYT | cyt-18 | tyrosine--tRNA ligase precursor, mitochondrial |
| SYWM_CAEEL (T15761) | — | Probable tryptophanyl-tRNA synthetase, mitochondrial (tryptophan--tRNA ligase) (TRPRS) |
| THTR_MOUSE (NP033463) | Tst | thiosulfate sulfortransferase |
| U80034 (NP005923) | MIPEP | mitochondrial intermediate peptidase |
| U82328 (NP003468) | PDX1 | pyruvate dehydrogenase complex protein X subunit precursor |
| XNHUDM (NP002071) | GOT2 | aspartate transaminase precursor, mitochondrial |
| XNHUO (NP000265) | OAT | ornithine--oxo-acid transaminase precursor |
| XNHUSP (NP000021) | AGXT | serine--pyruvate aminotransferase (SPT) (alanine--glyoxylate aminotransferase) (AGT) |
| XNMSO (AAH08119) | Oat | ornithine--oxo-acid transaminase precursor |
| XXHU | DLAT | dihydrolipoamide S-acetyltransferase precursor (fragment) |
| YAL044c (P39726) | GCV3 | GCV3—glycine decarboxylase, subunit H |
| YBL022c (NP009531) | PIM1 | PIM1—ATP-dependent protease, mitochondrial |
| YBL038w (NP009515) | MRPL16 | MRPL16—ribosomal protein of the large subunit, mitochondrial |
| YBL080c (NP009473) | PET112 | PET112—required to maintain rho+ mitochondrial DNA |
| YBL090w (NP009463) | MRP21 | MRP21—Mitochondrial ribosomal protein |
| YBR120c (NP009678) | CBP6 | CBP6—apo-cytochrome B pre-mRNA processing protein |
| YBR122c (CAA55624) | MRPL36 | MRPL36—ribosomal protein YmL36 precursor, mitochondrial |
| YBR146w (NP009704) | MRPS9 | MRPS9—ribosomal protein S9 precursor, mitochondrial |
| YBR221c (NP009780) | PDB1 | PDB1—pyruvate dehydrogenase (lipoamide) beta chain precursor |
| YBR227c (NP009786) | MCX1 | MCX1—ClpX homologue in mitochondria |
| YBR251w (NP009810) | MRPS5 | MRPS5—ribosomal protein S5, mitochondrial |
| YBR268w (NP009827) | MRPL37 | MRPL37—ribosomal protein YmL37, mitochondrial |
| YBR282w (NP009841) | MRPL27 | MRPL27—ribosomal protein YmL27 precursor, mitochondrial |
| YCR003w (NP009929) | MRPL32 | MRPL32—ribosomal protein YmL32, mitochondrial |
| YCR024c (NP009953) | — | asn-tRNA synthetase, mitochondrial |
| YCR028c-a (NP009958) | RIM1 | RIM1—ssDNA-binding protein, mitochondrial |
| YCR046c (NP009975) | IMG1 | IMG1—ribosomal protein, mitochondrial |
| YDL202w (NP010079) | MRPL11 | MRPL11—ribosomal protein of the large subunit, mitochondrial |
| YDR148c (NP010432) | KGD2 | KGD2—2-oxoglutarate dehydrogenase complex E2 component |
| YDR194c (NP010480) | MSS116 | MSS116—RNA helicase of the DEAD box family, mitochondrial |
| YDR462w (NP010750) | MRPL28 | MRPL28—ribosomal protein of the large subunit (YmL28), mitochondrial |
| YFL018c (NP116635) | LPD1 | LPD1—dihydrolipoamide dehydrogenase precursor |
| YGR244c (NP011760) | LSC2 | succinate-CoA ligase beta subunit |
| YHR008c (NP011872) | SOD2 | SOD2—superoxide dismutase (Mn) precursor, mitochondrial |
| YIL070c (NP012194) | MAM33 | MAM33—mitochondrial acidic matrix protein |
| YJL096w (CAA89390) | MRPL49 | MRPL49—ribosomal protein YmL49, mitochondrial |
| YJR113c (NP012647) | RSM7 | RSM7—similarity to bacterial, chloroplast and mitochondrial ribosomal protein S7 |
| YKL040c (NP012884) | NFU1 | NFU1—iron homeostasis |
| YLL027w (NP013073) | ISA1 | ISA1—mitochondrial protein required for normal iron metabolism |
| YLR059c (NP013160) | REX2 | REX2—putative 3'-5' exonuclease |
| YML110c (NP013597) | COQ5 | COQ5—ubiquinone biosynthesis, methyltransferase |
| YMR062c (NP013778) | ECM40 | ECM40—acetylornithine acetyltransferase |
| YMR072w (NP013788) | ABF2 | ABF2—high mobility group protein |
| YOL095c (NP014546) | HMI1 | HMI1—mitochondrial DNA helicase |
| YOR040w (NP014683) | GLO4 | GLO4—glyoxalase II (hydroxyacylglutathione hydrolase) |
| YOR142w (NP014785) | LSC1 | LSC1—succinate-CoA ligase alpha subunit |
| YPL118w (NP015207) | MRP51 | MRP51—strong similarity to S. kluyveri hypothetical protein |
| YPL135w (NP015190) | ISU1 | ISU1—protein with similarity to iron-sulfur cluster nitrogen fixation proteins |
| YPL252c (NP015071) | YAH1 | YAH1—similarity to adrenodoxin and ferrodoxin |
| YPL262w (NP015061) | FUM1 | FUM1—fumarate hydratase |
| YPR047w (CAA89167) | MSF1 | MSF1—phenylalanine--tRNA ligase alpha chain, mitochondrial |
| YPR067w (NP015392) | ISA2 | ISA2—mitochondrial protein required for iron metabolism | vii. Chloroplast Targeting

In another embodiment, modified compositions disclosed herein specifically deliver polypeptides to chloroplasts by including a chloroplast localization signal or domain. For chloroplasts, several amino-terminal targeting signals have been deduced are known in the art. The chloroplast is a photosynthetic organelle in eukaryotes with a double surrounding membrane. The fluid inside the double-membrane is called the stroma. The chloroplast has a nucleoid region to house its circular, naked DNA. The stroma is also the site of the Calvin Cycle. The Calvin Cycle is the series of enzyme-catalyzed chemical reactions that produce carbohydrates and other compounds from carbon dioxide.

Within the stroma are tiny membrane sacs called thylakoids. The sacs are stacked in groups. Each group is called a granum. There are many grana in each chloroplast. The thylakoid membranes are the site of photosynthetic light reactions. The thylakoids have intrinsic and extrinsic proteins, some with special prosthetic groups, allowing for electrons to be moved from protein complex to protein complex. These proteins constitute an electron transport system sometimes known as the Z-scheme.

The prosthetic group for two critical membrane proteins (P680 and P700) is a chlorophyll a pigment molecule. These chlorophyll-binding proteins give the thylakoids an intense green color. The many thylakoids in a chloroplast give the chloroplast a green color. The many chloroplasts in a leaf mesophyll cell give that cell a green color. The many mesophyll cells in a leaf give the leaf a green color. The chlorophyll molecule absorbs light energy and an electron is boosted within the electron cloud in a resonating chemical structure surrounding a magnesium ion. This excited electron is removed by the surrounding electron transport proteins in the membrane. The movement of these electrons, and accompanying protons, results ultimately in the trapping of energy in a phosphate bond in ATP. The thylakoid is thus the location for light absorption and ATP synthesis. The stroma uses the ATP to store the trapped energy in carbon-carbon bonds of carbohydrates. Some chloroplasts show developing starch grains. These represent complex polymers of carbohydrates for long-term storage.

Given the bioenergetic functions of chloroplasts, the ability to introduce exogenous polypeptides may lead to plants with increased viability in otherwise hostile environments and increased efficiency of photosynthesis. Thus, other embodiments are directed to the modification of chloroplasts for more effective biosynthesis strategies for commercial compounds.

TABLE 2

Targeting Signals for Cell Types or Cell States.

| Cell Surface Antigen/Cell Type | Cell Ligand |
|---|---|
| Airway cells | Surfactant proteins A and B |
| Arterial wall | Artery wall binding peptide |
| ASGP receptor | Asialoglycoproteins |
| ASGP receptor | Synthetic galactosylated ligands |
| Carbohydrates | Lectins |
| CD3 | Anti-CD 3 |
| CD5 | Anti-CD 5 |
| CD44 | hyaluronic acid fragments |
| CD117 | Steel factor, Anti CD117 |
| EGF-R | EGF, EGF peptide Anti EGF-R, TGF-alpha |
| ErbB2 | anti ErbB2 |
| FcR | IgG |
| FGF2-R | basic FGF |
| Folate receptor | Folate |
| Hepatocyte basolateral surface | Malarial circumsporozoite protein |
| Her2 | Anti HER2 |
| Insulin receptor | Insulin |
| Integrin | RGD peptide |
| LDL receptor family (hepatocytes) | Receptor associated protein (RAP) |
| Mannose receptor (macrophages) | Synthetic ligands, mannosylated |
| Nerve growth factor (NGF) receptor TrkA | NGF serived synthetic peptide |
| Neuroblastoma | Antibody ChCE7 |
| Ovarian carcinoma cell surface antigen OA3 | Antibody OV-TL16 Fab' fragment |
| PECAM (lung endothelium) | anti-PECAM antibody |
| Poly-immunoglobulin receptor | Anti-secretory component peptide ligand |
| Serpin-enzyme receptor | |
| Surface immunoglobulin | Anti-IgG, Anti-idiotype |

TABLE 2-continued

Targeting Signals for Cell Types or Cell States.

| Cell Surface Antigen/Cell Type | Cell Ligand |
|---|---|
| Thrombomodulin | Anti-thrombomodulin |
| Tn carbohydrate | Anti-Tn |
| Transferrin receptor | Transferrin |
| Airway cells | Surfactant proteins A and B |
| Arterial wall | Artery wall binding peptide |
| ASGP receptor | Asialoglycoproteins |
| ASGP receptor | Synthetic galactosylated ligands |
| Carbohydrates | Lectins |

3. Increasing Mitochondrial Biogenesis and OXPHOS

Figure 1B:
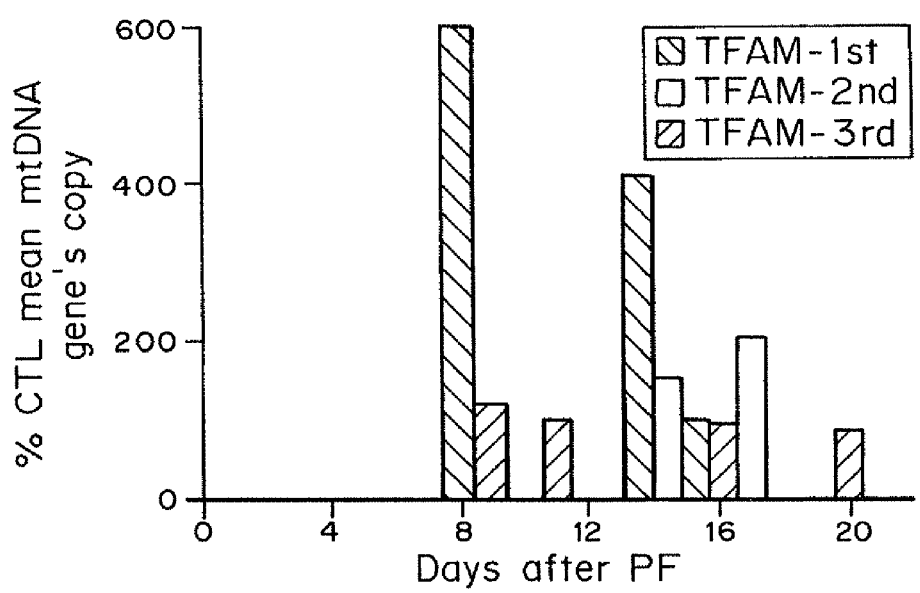
Figure 1C:
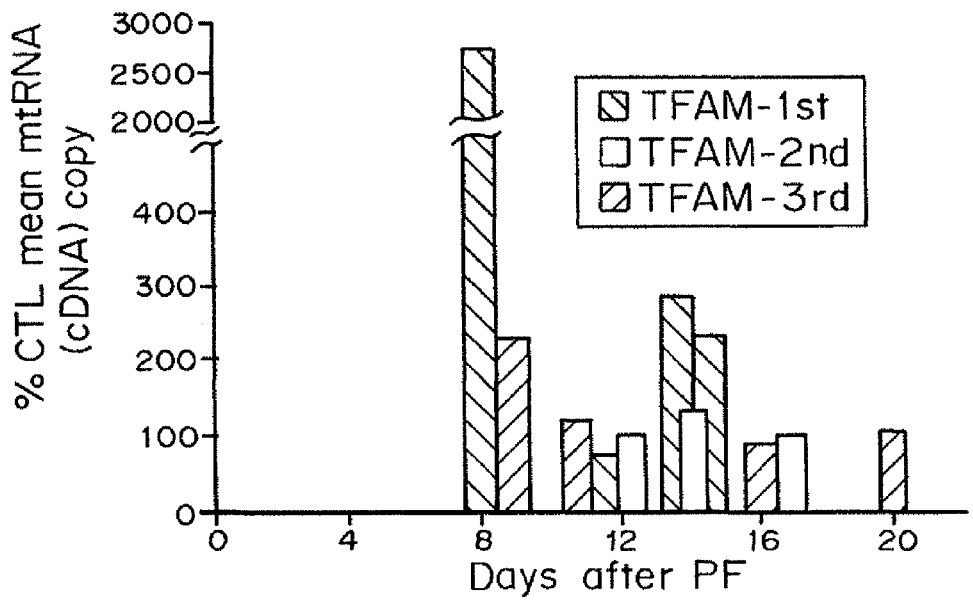

Embodiments of the present disclosure provide compositions and methods applicable to increasing mitochondrial biogenesis and oxidative metabolism. Cell dysfunction as a consequence of reduced mitochondrial biogenesis and/or oxidative metabolism can also be treated or reduced using the disclosed compositions and methods. For example, SH-SY5Y neuroblastoma cybrid cells carrying a G11778A mtDNA mutation in the ND4 gene from a patient afflicted with Leber's Hereditary Optic Neuropathy (LHON) were treated with mitochondrially targeted transducible TFAM (MTD-TFAM) or buffer control. Simultaneous "high-resolution" oximetry-respiration experiments using intact cells metabolizing glucose were conducted. The basal respiration values were depicted as a function of the same number of live cells expressed as a percentage of the corresponding buffer control cell values at each of the time points. Treatment with MTD-TFAM caused a time-dependent, reversible increase in basal respiration rates that reached a maximal ~3-fold increase over control samples at around 2 weeks (FIGS. 1A-C).

Figure 2:
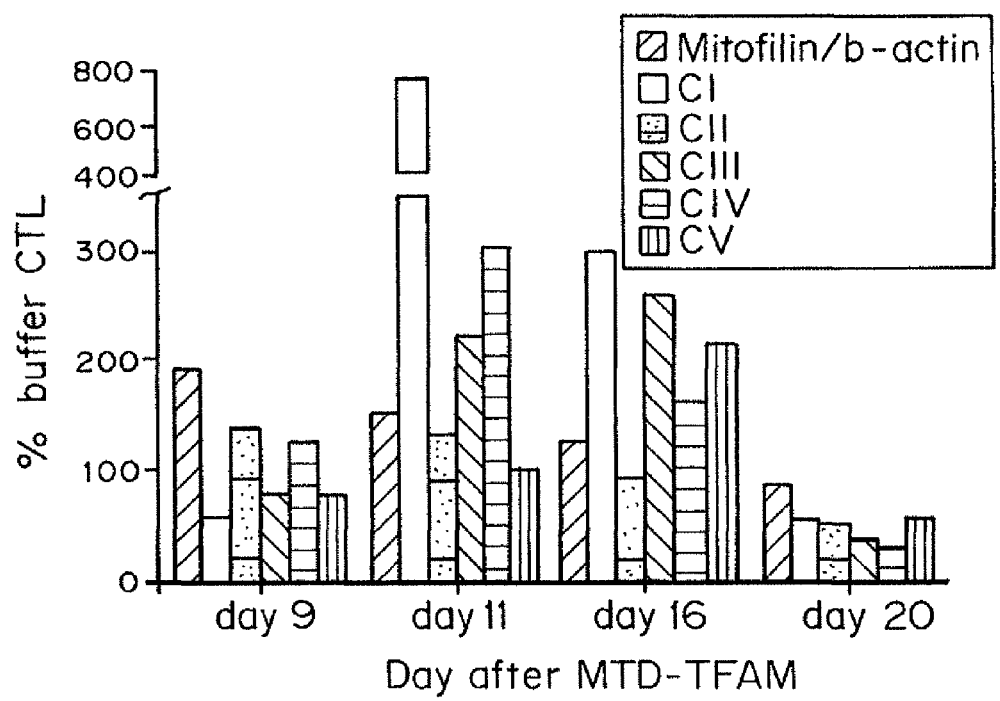
FIG. 2 depicts a bar graph of percent buffer control of the mitofilin/b-actin, CI, CII, CIII, CIV, and CV versus days after treatment with recombinant TFAM.
Figure 3A:
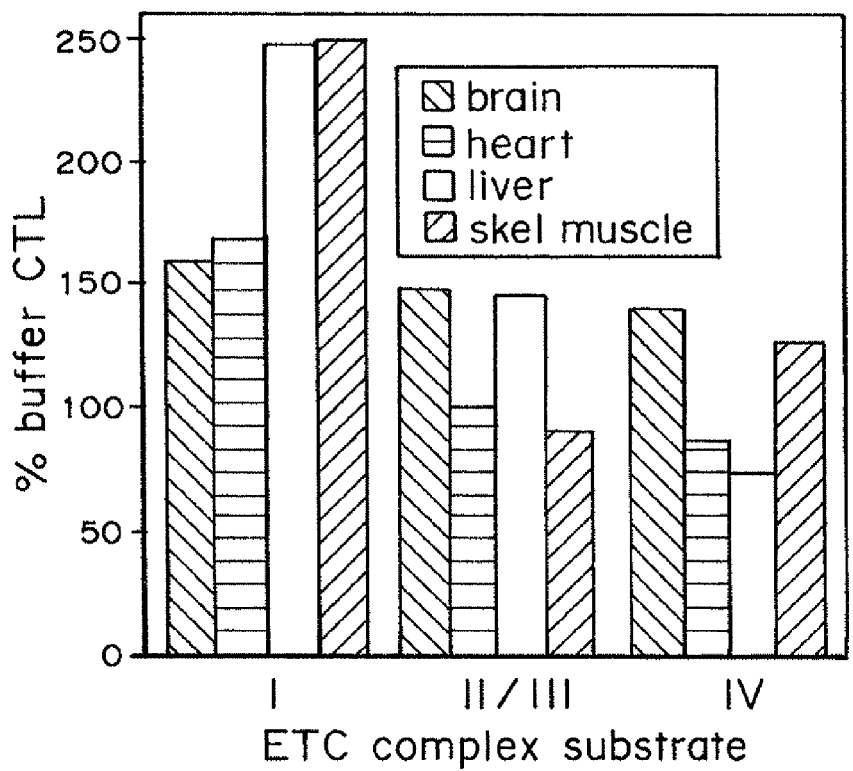
FIG. 3A shows a bar graph of percent buffer control of oxidative metabolism in brain, heart, liver, and skeletal muscle.
Figure 3B:
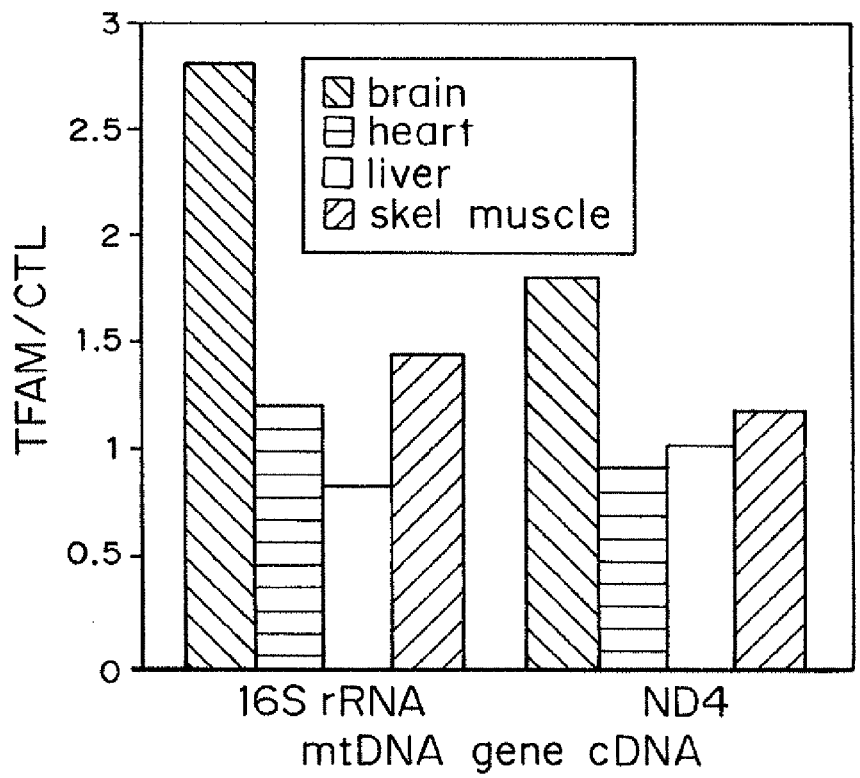
FIG. 3B shows a bar graph of TFAM/control versus mtDNA gene cDNA.

Because TFAM is a recognized essential factor for mitochondrial genome replication and transcription, MTD-TFAM exposure may be increasing mitochondrial gene replication, transcription and translation into respiratory proteins. Multiplex qPCR for several mitochondrial genes show substantial increases in mitochondrial gene copy numbers in both DNA and RNA (cDNA) following treatment with MTD-TFAM. Levels of multiple individual ETC proteins were assessed in treated cells using Western blots. Western blot analysis revealed that the relative mitochondrial mass in cells, expressed as a ratio of the outer mitochondrial membrane protein mitofilin to that of cytosolic beta actin, doubled (1.9-fold) in MTD-TFAM treated cells (FIG. 2). The levels of a mtDNA-encoded (CIV, subunit 2) and multiple nuclear genome-encoded ETC proteins from several complexes also increased substantially and reversibly in the MTD-TFAM treated cells with the greatest overall increases observed in complex I at day 11 (FIG. 2). The increase in respiration in cells was mirrored in animals. Normal adult male mice were treated with I.P. injections of MTD-TFAM or buffer control. Respiration was studied in mitochondrial preparations from brain, heart, skeletal muscle, kidney and liver. Treated mice showed increased respiration across tissues in the relative State 3 (+ADP) respiration rates for individual complexes (FIGS. 3A-3B). Thus the embodiments provided in the present disclosure enable methods to increase mitochondrial biogenesis and or mitochondrial oxidative metabolism.

4. Genetic Diseases or Syndromes

Embodiments of the present disclosure provide compositions and methods applicable for therapeutic protocols and the treatment of gene related diseases or disorders where mitochondrial dysfunction is primary event or secondary to the cause. Cell mitochondrial dysfunction can also be treated or reduced using the disclosed compositions and methods. In particular, diseases producing mitochondrial dysfunction are specifically targeted. Diseases where improved mitochondrial function might prove therapeutic are also disclosed. The disease can be in children, for example individuals less that 18 years of age, typically less than 12 years of age, or adults, for example individuals 18 years of age or more. Thus, embodiments of the present disclosure are directed to treating a host diagnosed with a disease, in particular a genetic disease, by treating the host with a transducible protein capable of reducing mitochondrial dysfunction or improving mitochondrial function.

Suitable genetic based diseases that can be treated with the compositions disclosed herein include but are not limited to:

Mitochondrial Disease:

Alpers Disease; Barth syndrome; β-oxidation defects; carnitine-acyl-carnitine deficiency; carnitine deficiency; co-enzyme Q10 deficiency; Complex I deficiency; Complex II deficiency; Complex III deficiency; Complex IV deficiency; Complex V deficiency; cytochrome c oxidase (COX) deficiency, LHON—Leber Hereditary Optic Neuropathy; MM W Mitochondrial Myopathy; LIMM—Lethal Infantile Mitochondrial Myopathy; MMC—Maternal Myopathy and Cardiomyopathy; NARP—Neurogenic muscle weakness, Ataxia, and Retinitis Pigmentosa; Leigh Disease; FICP—Fatal Infantile Cardiomyopathy Plus, a MELAS-associated cardiomyopathy; MELAS Mitochondrial Encephalomyopathy with Lactic Acidosis and Strokelike episodes; LDYT—Leber's hereditary optic neuropathy and Dystonia; MERRF—Myoclonic Epilepsy and Ragged Red Muscle Fibers; MHCM—Maternally inherited Hypertrophic CardioMyopathy; CPEO—Chronic Progressive External Ophthalmoplegia; KSS—Kearns Sayre Syndrome; DM—Diabetes Mellitus; DMDF Diabetes Mellitus+DeaFness; CIPO—Chronic Intestinal Pseudoobstruction with myopathy and Ophthalmoplegia; DEAF—Maternally inherited DEAFness or aminoglycoside-induced DEAFness; PEM—Progressive encephalopathy; SNHL—SensoriNeural Hearing Loss; Encephalomyopathy; Mitochondrial cytopathy; Dilated Cardiomyopathy; GER—Gastrointestinal Reflux; DEMCHO—Dementia and Chorea; AMDF—Ataxia, Myoclonus; Exercise Intolerance; ESOC Epilepsy, Strokes, Optic atrophy, & Cognitive decline; FBSN Familial Bilateral Striatal Necrosis; FSGS Focal Segmental Glomerulosclerosis; LIMM Lethal Infantile Mitochondrial Myopathy; MDM Myopathy and Diabetes Mellitus; MEPR Myoclonic Epilepsy and Psychomotor Regression; MERME MERRF/MELAS overlap disease; MHCM Maternally Inherited Hypertrophic CardioMyopathy; MICM Maternally Inherited Cardiomyopathy; MILS Maternally Inherited Leigh Syndrome; Mitochondrial Encephalocardiomyopathy; Multisystem Mitochondrial Disorder (myopathy, encephalopathy, blindness, hearing loss, peripheral neuropathy); NAION Nonarteritic Anterior Ischemic Optic Neuropathy; NIDDM Non-Insulin Dependent Diabetes Mellitus; PEM Progressive Encephalopathy; PME Progressive Myoclonus Epilepsy; RTT Rett Syndrome; SIDS Sudden Infant Death Syndrome; MIDD Maternally Inherited Diabetes and Deafness; and MODY Maturity-Onset Diabetes of the Young.

Nuclear Disease:

Muscular Dystrophies, Ellis-van Creveld syndrome, Marfan syndrome, Myotonic dystrophy, Spinal muscular atrophy, Achondroplasia, Amyotrophic lateral sclerosis, Charcot-Marie-Tooth syndrome, Cockayne syndrome, Diastrophic dysplasia, Duchenne muscular dystrophy, Ellis-van Creveld syndrome, Fibrodysplasia ossificans progressive, Alzheimer disease, Angelman syndrome, Epilepsy, Essential tremor, Fragile X syndrome, Friedreich's ataxia, Huntington disease, Niemann-Pick disease, Parkinson disease, Prader-Willi syndrome, Rett syndrome, Spinocerebellar atrophy, Williams syndrome, Ataxia telangiectasia, Anemia, sickle cell, Burkitt lymphoma, Gaucher disease, Hemophilia, Leukemia, Paroxysmal nocturnal hemoglobinuria, Porphyria, Thalassemia, Crohn's disease, Alpha-1-antitrypsin deficiency, Cystic fibrosis, Deafness, Pendred syndrome, Glaucoma, Gyrate atrophy of the choroid and retina, Adrenal hyperplasia, Adrenoleukodystrophy, Cockayne syndrome, Long QT syndrome, Immunodeficiency with hyper-IgM, Alport syndrome, Ellis-van Creveld syndrome, Fibrodysplasia ossificans progressive, Waardenburg syndrome, Werner syndrome.

Infectious Disease:

Viral—AIDS, AIDS Related Complex, Chickenpox (Varicella), Common cold, Cytomegalovirus Infection, Colorado tick fever, Dengue fever, Ebola haemorrhagic fever, Epidemic parotitis, Flu, Hand, foot and mouth disease, Hepatitis—Herpes simplex, Herpes zoster, HPV, Influenza, Lassa fever, Measles, Marburg haemorrhagic fever, Infectious mononucleosis, Mumps, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease—Yellow fever; Bacterial—Anthrax, Bacterial Meningitis, Brucellosis, Bubonic plague, Campylobacteriosis, Cat Scratch Disease, Cholera, Diphtheria, Epidemic Typhus, Gonorrhea, Hansen's Disease, Legionellosis, Leprosy, Leptospirosis, Listeriosis, Lyme Disease, Melioidosis, MRSA infection, Nocardiosis, Pertussis, Pneumococcal pneumonia, Psittacosis, Q fever, Rocky Mountain Spotted Fever or RMSF, Salmonellosis, Scarlet Fever, Shigellosis, Syphilis, Tetanus, Trachoma, Tuberculosis, Tularemia, Typhoid Fever, Typhus, Whooping Cough; Parasitic—African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trypanosomiasis.

Cancers:

Breast and ovarian cancer, Burkitt lymphoma, Chronic myeloid leukemia, Colon cancer, Lung cancer, Malignant melanoma, Multiple endocrine neoplasia, Neurofibromatosis, p53 LieFrauMeni, Pancreatic cancer, Prostate cancer, retinoblastoma, von Hippel-Lindau syndrome, Polycystic kidney disease, Tuberous sclerosis.

Metabolic Disorders:

Adrenoleukodystrophy, Atherosclerosis, Best disease, Gaucher disease, Glucose galactose malabsorption, Gyrate atrophy, Juvenile onset diabetes, Obesity, Paroxysmal nocturnal hemoglobinuria, Phenylketonuria, Refsum disease, Tangier disease, Tay-Sachs disease, Adrenoleukodystrophy, Type 2 Diabetes, Gaucher disease, Hereditary hemochromatosis, Lesch-Nyhan syndrome, Maple syrup urine disease, Menkes syndrome, Niemann-Pick disease, Pancreatic cancer, Prader-Willi syndrome, Porphyria, Refsum disease, Tangier disease, Wilson's disease, Zellweger syndrome, progerias, SCID.

Autoimmune Disorders:

Autoimmune polyglandular syndrome, lupus, type I diabetes, scleroderma, multiple sclerosis, Crohn's disease, chronic active hepatitis, rheumatoid arthritis, Graves' disease, myasthenia gravis, myositis, antiphospholipid syndrome (APS), uveitis, polymyositis, Raynaud's phenomenon, and demyelinating neuropathies, and rare disorders such as polymyalgia rheumatica, temporal arteritis, Sjogren's syndrome, Bechet's disease, Churg-Strauss syndrome, and Takayasu's arteritis.

Inflammatory Disorders:

Alopecia, Diastrophic dysplasia, Ellis-van Creveld syndrome, Asthma, Arthritis, including osteoarthritis, rheumatoid arthritis, and spondyloarthropathies.

Age-Related Disorders:

Alzheimer Disease, Parkinson's Disease, Atherosclerosis, Age-Related Macular Degeneration, Age-related Osteoporosis.

The disclosed methods and compositions can also be used to treat, manage, or reduce symptoms associated with aging, in tissue regeneration/regenerative medicine, stem cell transplantation, cognitive enhancement, performance enhancement, and cosmetic alterations to human or non-human animals.

9. Obesity and Food Consumption

Figure 4:
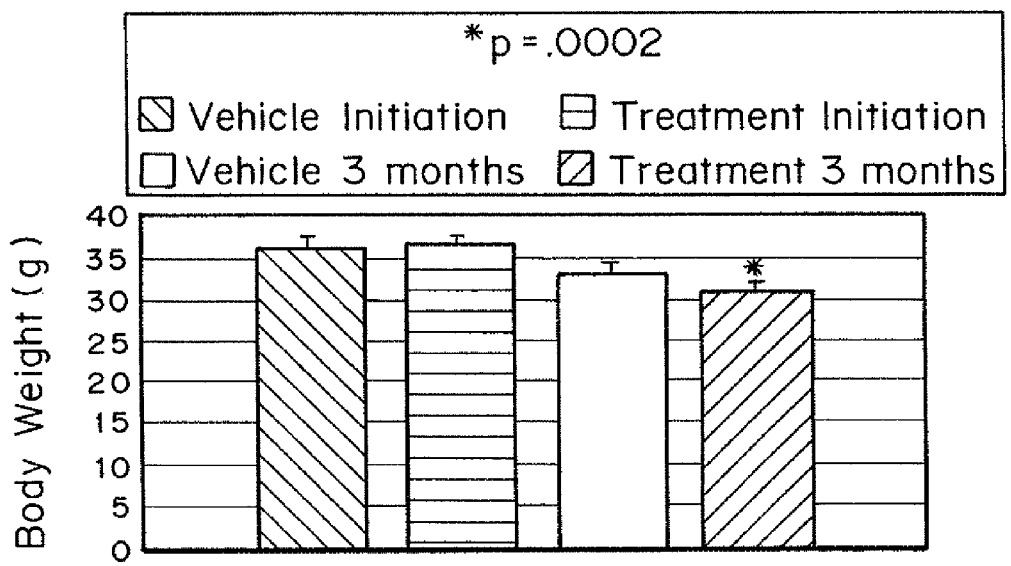
FIG. 4 shows a bar graph of body weight (grams) in mice treated with vehicle, recombinant TFAM, vehicle for 3 months, and recombinant TFAM over 3 months.
Figure 5:
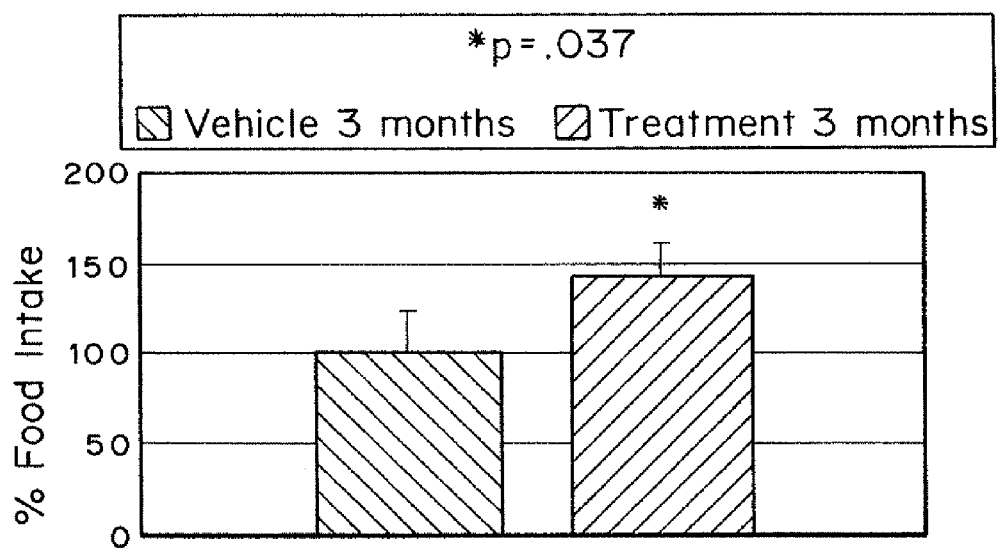
FIG. 5 shows a bar graph of percent food intake in mice injected with recombinant TFAM or vehicle over three months.

Embodiments of the present disclosure provide compositions and methods applicable to reducing obesity and/or increasing food intake. For example, 50 mice (25 vehicle control and 25 MTD-TFAM treated) were monitored for food intake and weight over a 3 month time interval during which saline or MTD-TFAM were injected IP on a monthly basis for a total of 3 injections, each. Mouse weight at the initiation of the study did not vary. Food intake was measured on a weekly basis. At the conclusion of the study, MTD-TFAM treated mice had statistically significant ($p=0.0002$) weight loss despite having consumed 43% more food than control animals over the course of the study ($p=0.037$) (FIGS. 4 and 5). In FIG. 5, 50 mice (25 vehicle control and 25 MTD—TFAM treated) were monitored for food intake over a 3 month time interval during which saline or MTD-TFAM were injected IP on a monthly basis for a total of 3 injections, each. Mouse weight at the initiation of the study did not vary. Food intake was measured on a weekly basis. At the conclusion of the study, MTD-TFAM treated mice had a statistically significant increase in food consumed of 43% over control animals over the course of the study ($p=0.037$). Thus, the disclosed methods can be used to treat obesity and/or increase food intake.

10. Administration

The compositions provided herein may be administered in a physiologically acceptable carrier to a host. Preferred methods of administration include systemic or direct administration to a cell. The compositions can be administered to a cell or patient, as is generally known in the art for protein therapies. One embodiment provides a pharmaceutical composition consisting essentially of a recombinant polypeptide having a polynucleotide-binding domain, a targeting domain, and a protein transduction domain and a pharmaceutically acceptable carrier or excipient. Preferably the polynucleotide-binding domain includes TFAM or a fragment thereof capable of binding a polynucleotide. The composition includes an effective amount of the recombinant polypeptide to increase mitochondrial metabolism.

The modified complex compositions can be combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween®, Pluronics® or PEG.

The compositions of the present disclosure can be administered parenterally. As used herein, "parenteral administration" is characterized by administering a pharmaceutical composition through a physical breach of a subject's tissue. Parenteral administration includes administering by injection, through a surgical incision, or through a tissue-penetrating non-surgical wound, and the like. In particular, parenteral administration includes subcutaneous, intraperitoneal, intravenous, intraarterial, intramuscular, intrasternal injection, and kidney dialytic infusion techniques.

Parenteral formulations can include the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Parenteral administration formulations include suspensions, solutions, emulsions in oily or aqueous vehicles, pastes, reconsitutable dry (i.e. powder or granular) formulations, and implantable sustained-release or biodegradable formulations. Such formulations may also include one or more additional ingredients including suspending, stabilizing, or dispersing agents. Parenteral formulations may be prepared, packaged, or sold in the form of a sterile injectable aqueous or oily suspension or solution. Parenteral formulations may also include dispersing agents, wetting agents, or suspending agents described herein. Methods for preparing these types of formulations are known. Sterile injectable formulations may be prepared using non-toxic parenterally-acceptable diluents or solvents, such as water, 1,3-butane diol, Ringer's solution, isotonic sodium chloride solution, and fixed oils such as synthetic monoglycerides or diglycerides. Other parentally-administrable formulations include microcrystalline forms, liposomal preparations, and biodegradable polymer systems. Compositions for sustained release or implantation may include pharmaceutically acceptable polymeric or hydrophobic materials such as emulsions, ion exchange resins, sparingly soluble polymers, and sparingly soluble salts.

Pharmaceutical compositions may be prepared, packaged, or sold in a buccal formulation. Such formulations may be in the form of tablets, powders, aerosols, atomized solutions, suspensions, or lozenges made using known methods, and may contain from about 0.1% to about 20% (w/w) active ingredient with the balance of the formulation containing an orally dissolvable or degradable composition and/or one or more additional ingredients as described herein. Preferably, powdered or aerosolized formulations have an average particle or droplet size ranging from about 0.1 nanometers to about 200 nanometers when dispersed.

As used herein, "additional ingredients" include one or more of the following: excipients, surface active agents, dispersing agents, inert diluents, granulating agents, disintegrating agents, binding agents, lubricating agents, sweetening agents, flavoring agents, coloring agents, preservatives, physiologically degradable compositions (e.g., gelatin), aqueous vehicles, aqueous solvents, oily vehicles and oily solvents, suspending agents, dispersing agents, wetting agents, emulsifying agents, demulcents, buffers, salts, thickening agents, fillers, emulsifying agents, antioxidants, antibiotics, antifungal agents, stabilizing agents, and pharmaceutically acceptable polymeric or hydrophobic materials. Other "additional ingredients" which may be included in the pharmaceutical compositions are known. Suitable additional ingredients are described in Remington's Pharmaceutical Sciences, Mack Publishing Co., Genaro, ed., Easton, Pa. (1985).

Dosages and desired concentrations modified vectors disclosed herein in pharmaceutical compositions of the present disclosure may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

EXAMPLES

Example 1

Recombinant Constructs

In a preferred embodiment, the recombinant polypeptide has at least 80, 85, 90, 95, 97, 99, or 100% sequence identity to

```
                                              (SEQ ID NO: 18)
MRRRRRRRRRRRGEGDIMGEWGNEIFGAIAGFLGGEMLSRAVCGTSRQL

PPVLGYLGSRQSSVLASCPKKPVSSYLRFSKEQLPIFKAQNPDAKTTEL

IRRIAQRWRELPDSKKKIYQDAYRAEWQVYKE EISRFKEQLTPSQIMS

LEKEIMDKHLKRKAMTKKKELTLLGKPKRPRSAYNVYVAERFQEAKGDS

PQEKLKTVKENWKNLSDSEKELYIQHAKEDETRYHNEMKSWEEQMIEVG

RKDLLRRTIKKQRKYGAEEC
```

In another embodiment, the recombinant polypeptide is encoded by a nucleic acid having at least 80, 85, 90, 95, 97, 99, or 100% sequence identity to

```
                                              (SEQ ID NO: 19)
atgcggcgac gcagacgtcg tcgtcggcgg cgtcgcggcg agggtgatat tatgggtgaa tgggggaacg aaattttcgg agcgatcgct ggttttctcg gtggagaaat gttatcacgc gcggtatgtg gcaccagcag gcagctgcct ccagtccttg gctatctggg ttcccgccag tcatcggtgt tagcatcatg tccgaaaaaa cctgtctcgt cgtacctgcg cttctccaaa gagcagctgc cgatttttaa agcgcaaaat ccggatgcta aaacgactga actgattcgc cgcattgcac aacgctggcg cgaactcccg gacagtaaaa aaaaaattta tcaggacgcc tatcgggctg aatggcaggt ctataaagag gagatctcac gcttcaaaga acaattaacc ccgagtcaaa taatgtctct ggaaaaagaa atcatggata aacacttaaa acgaaaggcg atgacgaaga aaaagaact gaccctgcta ggtaaaccta agcgtccgcg ctctgcgtat aatgtgtacg tggcagaacg ttttcaggag gccaagggg attctccgca agaaaaactg aagaccgtca aagaaaattg gaaaaacctg tctgatagcg aaaaagaact gtacattcag cacgctaaag aagatgagac gcggtatcac aacgaaatga aatcttggga agagcagatg atcgaggtcg gtcggaagga tcttctccgt cgaaccatca aaaaacagcg taaatatgga gcagaagagt gctga
```

PTD-MLS-TFAM Sequence (PTD underlined; Plant Mitochondrial Localization Signal from *A. thaliana* malate dehydrogenase double underlined; TFAM dash underline) Peptide Sequence Length: 262 aa MRRRRRRRRRRRGEGDIMGEWGNEIFGAIAGFLGGEMFRSMLVRSSASAKQAVIRRSFSSVLASCPKKPVSSYLRFSKEQLPIFKAQNPDAKTTELIRRIAQRWRELPDSKKKIYQDAYRAEWQVYKEEISRFKEQLTPSQIMSLEKEIMDKHLRKAMTKKKELTLLGKPKRPRSAYNVYVAERFQEAKGDSPQEKLKTVKENWKNLSDSEKELYIQHAKEDETRYHNEMLSWEEQMIEVGRKDLLRRTIKKQRKYGAEEC (SEQ ID NO: 20)

Example 2

Construct Sequence Data

The 11 amino acid protein transduction domain (PTD) consisting of 11 arginines was cloned in frame to the antibody binding portion, domain B, of Protein A from Staphylococcus aureus. The PTD-Domain B coding sequence was cloned in tandem upstream of the TFAM coding sequence and cloned into a bacterial expression vector. The recombinant protein was expressed in bacteria and isolated. Purified protein was concentrated and protein concentration was assessed with the Bradford Assay (Biorad). Purified protein was analyzed with SDS-Page to verify purity.

PTD-PA-TFAM (PTD solid underline; Tandem Domain B of Protein A Antibody Binding Domain double underline; TFAM dash underline) peptide Length (332):

(SEQ ID NO: 17)
MRRRRRRRRRRRGEGDIMGEWGNEIFGAIAGFLGGEHDEAQQNAFYQVLNMPNLNADQRNGFIQSLKDDPSQSANVLGEAHDEAQQNAFYQVLNMPNLNADQRNGFIQSLKDDPSQSANVLGEAGEGSSVLASCPKKPVSSYLRFSKEQLPIFKAQNPDAKTTELIRRIAQRWRELPDSKKKIYQDAYRAEWQVYKEEISRFKEQLTPSQIMSLEKEIMDKHLKRKAMTKKKELTLLGKPKRPRSAYNVYVAERFQEAKGDSPQEKLKTVKENWKNLSDSEKELYIQHAKEDETRYHNEMKSWEEQMIEVGRKDLLRRTIKKQRKYGAEEC

Selected Model Organism Protein Similarities that can be Used in the Compositions and Methods Disclosed Herein:

| | Organism, Protein And Percent Identity And Length Of Aligned Region | | |
|---|---|---|---|
| *H. sapiens* | sp: Q00059—MTT1_HUMAN Transcription factor 1, mitochondrial precursor (MTTF1) | 100%/246 aa | (see ProtEST) |
| *M. musculus* | ref: NP_033386.1—transcription factor A, mitochondrial [*Mus musculus*] | 63%/237 aa | (see ProtEST) |
| *R. norvegicus*: | ref: NP_112616.1—transcription factor A, mitochondrial [*Rattus norvegicus*] | 64%/237 aa | (see ProtEST) |
| *A. thaliana* | ref: NP_192846.1—98b like protein [*Arabidopsis thaliana*] | 27%/189 aa | (see ProtEST) |
| *C. elegans* | ref: NP_501245.1—F45E4.9.p [*Caenorhabditis elegans*] | 27%/189 aa | (see ProtEST) |
| *D. melanogaster*: | ref: NP_524415.1—mitochondrial transcription factor A [*Drosophila melanogaster*] | 34%/183 aa | (see ProtEST) |

Sequence data for the sequences referenced herein are known in the art, for example in GenBank, and are incorporated by reference herein, in their entirety.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A fusion protein comprising a protein transduction domain, a mitochondrial localization signal and the mature Transcription Factor A-mitochondrial (TFAM) of SEQ ID NO:20.

2. The fusion protein of claim 1 wherein the protein transduction domain comprises 11 arginines.

3. The fusion protein of claim 1, wherein the mitochondrial localization signal is the mitochondrial localization signal of superoxide dismutase (Mn).

4. A fusion protein comprising SEQ ID NO:20, the fusion protein comprising a protein transduction domain, a mitochondrial localization signal, and mature TFAM, wherein the mitochondrial localization signal is the mitochondrial localization signal of superoxide dismutase (Mn) and wherein the N-terminal amino acid of SEQ ID NO:20 is deleted.

5. A fusion protein consisting of SEQ ID NO:18 with the N-terminal amino acid deleted.

* * * * *

SEQUENCE LISTING

<160> NUMBER OF SEQ ID NOS: 20

<210> SEQ ID NO 1
<211> LENGTH: 11
<212> TYPE: PRT
<213> ORGANISM: Human immunodeficiency virus

<400> SEQUENCE: 1

Tyr Gly Arg Lys Lys Arg Arg Gln Arg Arg Arg
1               5                   10

<210> SEQ ID NO 2
<211> LENGTH: 9
<212> TYPE: PRT
<213> ORGANISM: Human immunodeficiency virus

<400> SEQUENCE: 2

Arg Lys Lys Arg Arg Gln Arg Arg Arg
1               5

<210> SEQ ID NO 3
<211> LENGTH: 10
<212> TYPE: DNA
<213> ORGANISM: Artificial sequence
<220> FEATURE:
<223> OTHER INFORMATION: SOX9 DNA binding domain

<400> SEQUENCE: 3
agaacaatgg                                                          10

<210> SEQ ID NO 4
<211> LENGTH: 7
<212> TYPE: PRT
<213> ORGANISM: Artificial Sequence
<220> FEATURE:
<223> OTHER INFORMATION: Synthetic protein transduction domain

<400> SEQUENCE: 4

Arg Arg Arg Arg Arg Arg Arg
1               5

<210> SEQ ID NO 5
<211> LENGTH: 12
<212> TYPE: PRT
<213> ORGANISM: Artificial Sequence
<220> FEATURE:
<223> OTHER INFORMATION: Protein transduction domain

<400> SEQUENCE: 5

Arg Arg Gln Arg Arg Thr Ser Lys Leu Met Lys Arg
1               5                   10

<210> SEQ ID NO 6
<211> LENGTH: 27
<212> TYPE: PRT
<213> ORGANISM: Artificial Sequence
<220> FEATURE:
<223> OTHER INFORMATION: Protein transduction domain

<400> SEQUENCE: 6

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

```
<210> SEQ ID NO 7
<211> LENGTH: 29
<212> TYPE: PRT
<213> ORGANISM: Artificial Sequence
<220> FEATURE:
<223> OTHER INFORMATION: Protein transduction domain

<400> SEQUENCE: 7

Trp Glu Ala Lys Leu Ala Lys Ala Leu Ala Lys Ala Leu Ala Lys His
1               5                   10                  15

Leu Ala Lys Ala Leu Ala Lys Ala Leu Lys Cys Glu Ala
            20                  25

<210> SEQ ID NO 8
<211> LENGTH: 16
<212> TYPE: PRT
<213> ORGANISM: Artificial Sequence
<220> FEATURE:
<223> OTHER INFORMATION: Protein transduction domain

<400> SEQUENCE: 8

Arg Gln Ile Lys Ile Trp Phe Gln Asn Arg Arg Met Lys Trp Lys Lys
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Nuclear localization signal

<400> SEQUENCE: 9

Pro Lys Lys Lys Arg Lys Val
1               5

<210> SEQ ID NO 10
<211> LENGTH: 7
<212> TYPE: PRT
<213> ORGANISM: Artificial Sequence
<220> FEATURE:
<223> OTHER INFORMATION: Nuclear localization signal

<400> SEQUENCE: 10

Gly Lys Lys Arg Ser Lys Val
1               5

<210> SEQ ID NO 11
<211> LENGTH: 7
<212> TYPE: PRT
<213> ORGANISM: Artificial Sequence
<220> FEATURE:
<223> OTHER INFORMATION: Nuclear localization signal

<400> SEQUENCE: 11

Lys Ser Arg Lys Arg Lys Leu
1               5

<210> SEQ ID NO 12
<211> LENGTH: 19
<212> TYPE: PRT
<213> ORGANISM: Artificial Sequence
<220> FEATURE:
<223> OTHER INFORMATION: Nuclear localization signal

<400> SEQUENCE: 12

Lys Arg Pro Ala Ala Thr Lys Lys Ala Gly Gln Ala Lys Lys Lys Lys
1               5                   10                  15
```

Leu Asp Lys

<210> SEQ ID NO 13
<211> LENGTH: 20
<212> TYPE: PRT
<213> ORGANISM: Artificial Sequence
<220> FEATURE:
<223> OTHER INFORMATION: Nuclear localization signal

<400> SEQUENCE: 13

Arg Lys Lys Arg Lys Thr Glu Glu Glu Ser Pro Leu Lys Asp Lys Ala
1               5                   10                  15

Lys Lys Ser Lys
            20

<210> SEQ ID NO 14
<211> LENGTH: 20
<212> TYPE: PRT
<213> ORGANISM: Artificial Sequence
<220> FEATURE:
<223> OTHER INFORMATION: Nuclear localization signal

<400> SEQUENCE: 14

Lys Asp Cys Val Met Asn Lys His His Arg Asn Arg Cys Gln Tyr Cys
1               5                   10                  15

Arg Leu Gln Arg
            20

<210> SEQ ID NO 15
<211> LENGTH: 9
<212> TYPE: PRT
<213> ORGANISM: Artificial Sequence
<220> FEATURE:
<223> OTHER INFORMATION: Nuclear localization signal

<400> SEQUENCE: 15

Pro Ala Ala Lys Arg Val Lys Leu Asp
1               5

<210> SEQ ID NO 16
<211> LENGTH: 20
<212> TYPE: PRT
<213> ORGANISM: Artificial Sequence
<220> FEATURE:
<223> OTHER INFORMATION: Nuclear localization signal

<400> SEQUENCE: 16

Lys Lys Tyr Glu Asn Val Val Ile Lys Arg Ser Pro Arg Lys Arg Gly
1               5                   10                  15

Arg Pro Arg Lys
            20

<210> SEQ ID NO 17
<211> LENGTH: 331
<212> TYPE: PRT
<213> ORGANISM: Artificial Sequence
<220> FEATURE:
<223> OTHER INFORMATION: Synthetic PTD-PA-TFAM peptide construct

<400> SEQUENCE: 17

Met Arg Arg Arg Arg Arg Arg Arg Arg Arg Arg Gly Glu Gly Asp
1               5                   10                  15

Ile Met Gly Glu Trp Gly Asn Glu Ile Phe Gly Ala Ile Ala Gly Phe
            20                  25                  30

```
Leu Gly Gly Glu His Asp Glu Ala Gln Gln Asn Ala Phe Tyr Gln Val
            35                  40                  45

Leu Asn Met Pro Asn Leu Asn Ala Asp Gln Arg Asn Gly Phe Ile Gln
 50                  55                  60

Ser Leu Lys Asp Asp Pro Ser Gln Ser Ala Asn Val Leu Gly Glu Ala
 65                  70                  75                  80

His Asp Glu Ala Gln Gln Asn Ala Phe Tyr Gln Val Leu Asn Met Pro
                85                  90                  95

Asn Leu Asn Ala Asp Gln Arg Asn Gly Phe Ile Gln Ser Leu Lys Asp
            100                 105                 110

Asp Pro Ser Gln Ser Ala Asn Val Leu Gly Glu Ala Gly Glu Gly Ser
            115                 120                 125

Ser Val Leu Ala Ser Cys Pro Lys Lys Pro Val Ser Ser Tyr Leu Arg
            130                 135                 140

Phe Ser Lys Glu Gln Leu Pro Ile Phe Lys Ala Gln Asn Pro Asp Ala
145                 150                 155                 160

Lys Thr Thr Glu Leu Ile Arg Arg Ile Ala Gln Arg Trp Arg Glu Leu
                165                 170                 175

Pro Asp Ser Lys Lys Lys Ile Tyr Gln Asp Ala Tyr Arg Ala Glu Trp
            180                 185                 190

Gln Val Tyr Lys Glu Glu Ile Ser Arg Phe Lys Glu Gln Leu Thr Pro
            195                 200                 205

Ser Gln Ile Met Ser Leu Glu Lys Glu Ile Met Asp Lys His Leu Lys
            210                 215                 220

Arg Lys Ala Met Thr Lys Lys Glu Leu Thr Leu Leu Gly Lys Pro
225                 230                 235                 240

Lys Arg Pro Arg Ser Ala Tyr Asn Val Tyr Val Ala Glu Arg Phe Gln
                245                 250                 255

Glu Ala Lys Gly Asp Ser Pro Gln Glu Lys Leu Lys Thr Val Lys Glu
            260                 265                 270

Asn Trp Lys Asn Leu Ser Asp Ser Glu Lys Glu Leu Tyr Ile Gln His
            275                 280                 285

Ala Lys Glu Asp Glu Thr Arg Tyr His Asn Glu Met Lys Ser Trp Glu
            290                 295                 300

Glu Gln Met Ile Glu Val Gly Arg Lys Asp Leu Leu Arg Arg Thr Ile
305                 310                 315                 320

Lys Lys Gln Arg Lys Tyr Gly Ala Glu Glu Cys
                325                 330

<210> SEQ ID NO 18
<211> LENGTH: 264
<212> TYPE: PRT
<213> ORGANISM: Artificial Sequence
<220> FEATURE:
<223> OTHER INFORMATION: Synthetic fusion protein

<400> SEQUENCE: 18

Met Arg Arg Arg Arg Arg Arg Arg Arg Arg Gly Glu Gly Asp
1               5                   10                  15

Ile Met Gly Glu Trp Gly Asn Glu Ile Phe Gly Ala Ile Ala Gly Phe
                20                  25                  30

Leu Gly Gly Glu Met Leu Ser Arg Ala Val Cys Gly Thr Ser Arg Gln
            35                  40                  45

Leu Pro Pro Val Leu Gly Tyr Leu Gly Ser Arg Gln Ser Ser Val Leu
 50                  55                  60
```

```
Ala Ser Cys Pro Lys Lys Pro Val Ser Ser Tyr Leu Arg Phe Ser Lys
 65                  70                  75                  80

Glu Gln Leu Pro Ile Phe Lys Ala Gln Asn Pro Asp Ala Lys Thr Thr
                 85                  90                  95

Glu Leu Ile Arg Arg Ile Ala Gln Arg Trp Arg Glu Leu Pro Asp Ser
            100                 105                 110

Lys Lys Lys Ile Tyr Gln Asp Ala Tyr Arg Ala Glu Trp Gln Val Tyr
        115                 120                 125

Lys Glu Glu Ile Ser Arg Phe Lys Glu Gln Leu Thr Pro Ser Gln Ile
130                 135                 140

Met Ser Leu Glu Lys Glu Ile Met Asp Lys His Leu Lys Arg Lys Ala
145                 150                 155                 160

Met Thr Lys Lys Lys Glu Leu Thr Leu Leu Gly Lys Pro Lys Arg Pro
                165                 170                 175

Arg Ser Ala Tyr Asn Val Tyr Val Ala Glu Arg Phe Gln Glu Ala Lys
            180                 185                 190

Gly Asp Ser Pro Gln Glu Lys Leu Lys Thr Val Lys Glu Asn Trp Lys
        195                 200                 205

Asn Leu Ser Asp Ser Glu Lys Glu Leu Tyr Ile Gln His Ala Lys Glu
    210                 215                 220

Asp Glu Thr Arg Tyr His Asn Glu Met Lys Ser Trp Glu Glu Gln Met
225                 230                 235                 240

Ile Glu Val Gly Arg Lys Asp Leu Leu Arg Arg Thr Ile Lys Lys Gln
                245                 250                 255

Arg Lys Tyr Gly Ala Glu Glu Cys
            260

<210> SEQ ID NO 19
<211> LENGTH: 795
<212> TYPE: DNA
<213> ORGANISM: Artificial Sequence
<220> FEATURE:
<223> OTHER INFORMATION: Synthetic fusion nuclec acid encoding fusion
      protein

<400> SEQUENCE: 19
atgcggcgac gcagacgtcg tcgtcggcgg cgtcgcggcg agggtgatat tatgggtgaa      60
tgggggaacg aaattttcgg agcgatcgct ggttttctcg gtggagaaat gttatcacgc     120
gcggtatgtg gcaccagcag gcagctgcct ccagtccttg gctatctggg ttcccgccag     180
tcatcggtgt tagcatcatg tccgaaaaaa cctgtctcgt cgtacctgcg cttctccaaa     240
gagcagctgc cgattttaaa gcgcaaaat ccggatgcta aaacgactga actgattcgc      300
cgcattgcac aacgctggcg cgaactcccg gacagtaaaa aaaaatttta tcaggacgcc     360
tatcgggctg aatggcaggt ctataaagag gagatctcac gcttcaaaga acaattaacc     420
ccgagtcaaa taatgtctct ggaaaaagaa atcatggata acacttaaa acgaaaggcg      480 atgacgaaga aaaagaact gaccctgcta ggtaaaccta gcgtccgcg ctctgcgtat       540 aatgtgtacg tggcagaacg ttttcaggag gccaaggggg attctccgca agaaaaactg    600
aagaccgtca agaaaattg gaaaaacctg tctgatagcg aaaaagaact gtacattcag     660
cacgctaaag aagatgagac gcggtatcac aacgaaatga atcttggga gagcagatg      720 atcgaggtcg gtcggaagga tcttctccgt cgaaccatca aaaacagcg taaatatgga     780 gcagaagagt gctga                                                     795
```

```
<210> SEQ ID NO 20
<211> LENGTH: 262
<212> TYPE: PRT
<213> ORGANISM: Artificial Sequence
<220> FEATURE:
<223> OTHER INFORMATION: synthetic peptide: PTD-MLS-TFAM sequence

<400> SEQUENCE: 20

Met Arg Arg Arg Arg Arg Arg Arg Arg Arg Arg Gly Glu Gly Asp
1               5                   10                  15

Ile Met Gly Glu Trp Gly Asn Glu Ile Phe Gly Ala Ile Ala Gly Phe
            20                  25                  30

Leu Gly Gly Glu Met Phe Arg Ser Met Leu Val Arg Ser Ser Ala Ser
            35                  40                  45

Ala Lys Gln Ala Val Ile Arg Arg Ser Phe Ser Ser Val Leu Ala Ser
    50                  55                  60

Cys Pro Lys Lys Pro Val Ser Ser Tyr Leu Arg Phe Ser Lys Glu Gln
65                  70                  75                  80

Leu Pro Ile Phe Lys Ala Gln Asn Pro Asp Ala Lys Thr Thr Glu Leu
                85                  90                  95

Ile Arg Arg Ile Ala Gln Arg Trp Arg Glu Leu Pro Asp Ser Lys Lys
                100                 105                 110

Lys Ile Tyr Gln Asp Ala Tyr Arg Ala Glu Trp Gln Val Tyr Lys Glu
            115                 120                 125

Glu Ile Ser Arg Phe Lys Glu Gln Leu Thr Pro Ser Gln Ile Met Ser
    130                 135                 140

Leu Glu Lys Glu Ile Met Asp Lys His Leu Lys Arg Lys Ala Met Thr
145                 150                 155                 160

Lys Lys Lys Glu Leu Thr Leu Leu Gly Lys Pro Lys Arg Pro Arg Ser
                165                 170                 175

Ala Tyr Asn Val Tyr Val Ala Glu Arg Phe Gln Glu Ala Lys Gly Asp
                180                 185                 190

Ser Pro Gln Glu Lys Leu Lys Thr Val Lys Glu Asn Trp Lys Asn Leu
        195                 200                 205

Ser Asp Ser Glu Lys Glu Leu Tyr Ile Gln His Ala Lys Glu Asp Glu
    210                 215                 220

Thr Arg Tyr His Asn Glu Met Lys Ser Trp Glu Glu Gln Met Ile Glu
225                 230                 235                 240

Val Gly Arg Lys Asp Leu Leu Arg Arg Thr Ile Lys Lys Gln Arg Lys
                245                 250                 255

Tyr Gly Ala Glu Glu Cys
            260
```